United States Patent
Kimura et al.

(10) Patent No.: US 12,050,301 B2
(45) Date of Patent: Jul. 30, 2024

(54) MAGNETIC RESPONSE DISTRIBUTION VISUALIZATION DEVICE, SECURITY INSPECTION SYSTEM, AND MAGNETIC RESPONSE DISTRIBUTION VISUALIZATION METHOD

(71) Applicant: Integral Geometry Science Inc., Hyogo (JP)

(72) Inventors: Noriaki Kimura, Hyogo (JP); Kenjiro Kimura, Hyogo (JP); Yuki Mima, Hyogo (JP); Shogo Suzuki, Hyogo (JP)

(73) Assignee: INTEGRAL GEOMETRY SCIENCE INC., Hyogo (JP)

( * ) Notice: Subject to any disclaimer, the term of this patent is extended or adjusted under 35 U.S.C. 154(b) by 91 days.

(21) Appl. No.: 17/917,088

(22) PCT Filed: Mar. 31, 2021

(86) PCT No.: PCT/JP2021/014014
§ 371 (c)(1),
(2) Date: Oct. 5, 2022

(87) PCT Pub. No.: WO2021/205966
PCT Pub. Date: Oct. 14, 2021

(65) Prior Publication Data
US 2023/0152482 A1      May 18, 2023

(30) Foreign Application Priority Data
Apr. 8, 2020   (JP) .................. 2020-069616

(51) Int. Cl.
*G01V 3/10*      (2006.01)
*A61B 5/00*      (2006.01)
(Continued)

(52) U.S. Cl.
CPC ............... *G01V 3/10* (2013.01); *A61B 5/015* (2013.01); *G01R 33/0094* (2013.01);
(Continued)

(58) Field of Classification Search
CPC .......... G01V 3/10; G01V 3/081; A61B 5/015; A61B 5/742; G01R 33/028;
(Continued)

(56) References Cited

U.S. PATENT DOCUMENTS

2008/0054893 A1    3/2008   Humphreys et al.
2015/0323664 A1    11/2015  Wu et al.
(Continued)

FOREIGN PATENT DOCUMENTS

EP    0 740 822       7/2003
JP    2015-36679      2/2015

OTHER PUBLICATIONS

International Search Report (ISR) issued on Jun. 29, 2021 in International (PCT) Application No. PCT/JP2021/014014.
(Continued)

*Primary Examiner* — Raul J Rios Russo
(74) *Attorney, Agent, or Firm* — Wenderoth, Lind & Ponack, L.L.P.

(57) ABSTRACT

A magnetic response distribution visualization device includes: an induction circuit that induces a magnetic field component from outside a moving object; a sensor that senses a strength and a phase of the magnetic field at a plurality of points in times outside the moving object; and an information processing circuit that, based on a sensing result of the strength and the phase, a moving speed of the moving object, and a fundamental equation for magnetic fields, calculates a strength and a phase of the magnetic field at a vicinal position closer to the moving object than the sensor, and generates, based on a calculation result of the strength
(Continued)

and the phase, a magnetic response distribution image for security inspection that shows a distribution of a response of the moving object to the magnetic field component induced by the induction circuit.

18 Claims, 19 Drawing Sheets

(51) Int. Cl.
  *A61B 5/01* (2006.01)
  *G01R 33/00* (2006.01)
  *G01R 33/028* (2006.01)
  *G01R 33/10* (2006.01)
  *G01V 3/08* (2006.01)

(52) U.S. Cl.
  CPC ........... *G01R 33/028* (2013.01); *G01R 33/10* (2013.01); *G01V 3/081* (2013.01); *A61B 5/742* (2013.01)

(58) Field of Classification Search
  CPC .... G01R 33/0094; G01R 33/10; G01R 33/02; G01R 33/09; G01N 27/72
  USPC .......................................................... 324/239
  See application file for complete search history.

(56) References Cited

U.S. PATENT DOCUMENTS

2018/0011472 A1* 1/2018 Sun ...................... G05B 19/402
2019/0204116 A1* 7/2019 Rajamani ............... G01D 5/145
2022/0413066 A1* 12/2022 Kimura .............. G01R 33/0023

OTHER PUBLICATIONS

Extended European Search Report issued Apr. 9, 2024 in corresponding European Patent Application No. 21784096.6.

* cited by examiner

MAGNETIC RESPONSE DISTRIBUTION VISUALIZATION DEVICE, SECURITY INSPECTION SYSTEM, AND MAGNETIC RESPONSE DISTRIBUTION VISUALIZATION METHOD

TECHNICAL FIELD

The present disclosure relates to a magnetic response distribution visualization device and the like that generates an image showing a distribution of a response to an external field.

BACKGROUND ART

Currently, security checks are conducted at airports and other locations using millimeter wave technology. PTL 1 proposes, for example, a millimeter wave three dimensional holographic scan imaging apparatus that can improve scanning speed and accuracy.

CITATION LIST

Patent Literature

[PTL 1] Japanese Unexamined Patent Application Publication No. 2015-36679

SUMMARY OF INVENTION

Technical Problem

However, the presence of numerous obstacles that block millimeter waves, such as living bodies and metal cases, may make it difficult to properly detect target objects.

In view of this, the present disclosure provides a magnetic response distribution visualization device that can generate an image showing the distribution of the response of a moving object to an external field with high accuracy as an image to be used for security inspection.

Solution to Problem

A magnetic response distribution visualization device according to one aspect of the present disclosure includes: an induction circuit that induces, from outside a moving object, a magnetic field component that is a component of a magnetic field that satisfies a fundamental equation for magnetic fields; a sensor that senses a strength and a phase of the magnetic field including the magnetic field component altered by the moving object, at a plurality of points in time outside the moving object; and an information processing circuit that, based on a sensing result of the strength and the phase of the magnetic field, a moving speed of the moving object, and the fundamental equation for magnetic fields, calculates a strength and a phase of the magnetic field at a vicinal position closer to the moving object than the sensor, and generates, based on a calculation result of the strength and the phase of the magnetic field, a magnetic response distribution image that shows a distribution of a response of the moving object to the magnetic field component induced by the induction circuit and is used for security inspection.

These general or specific aspects may be implemented as a system, a device or apparatus, a method, an integrated circuit, a computer program, or a non-transitory computer-readable recording medium such a CD-ROM, or any combination thereof.

Advantageous Effects of Invention

According to one aspect of the present disclosure, it is possible to generate an image showing the distribution of the response of a moving object to an external field with high accuracy as an image to be used for security inspection.

DESCRIPTION OF EMBODIMENTS

Figure 1:
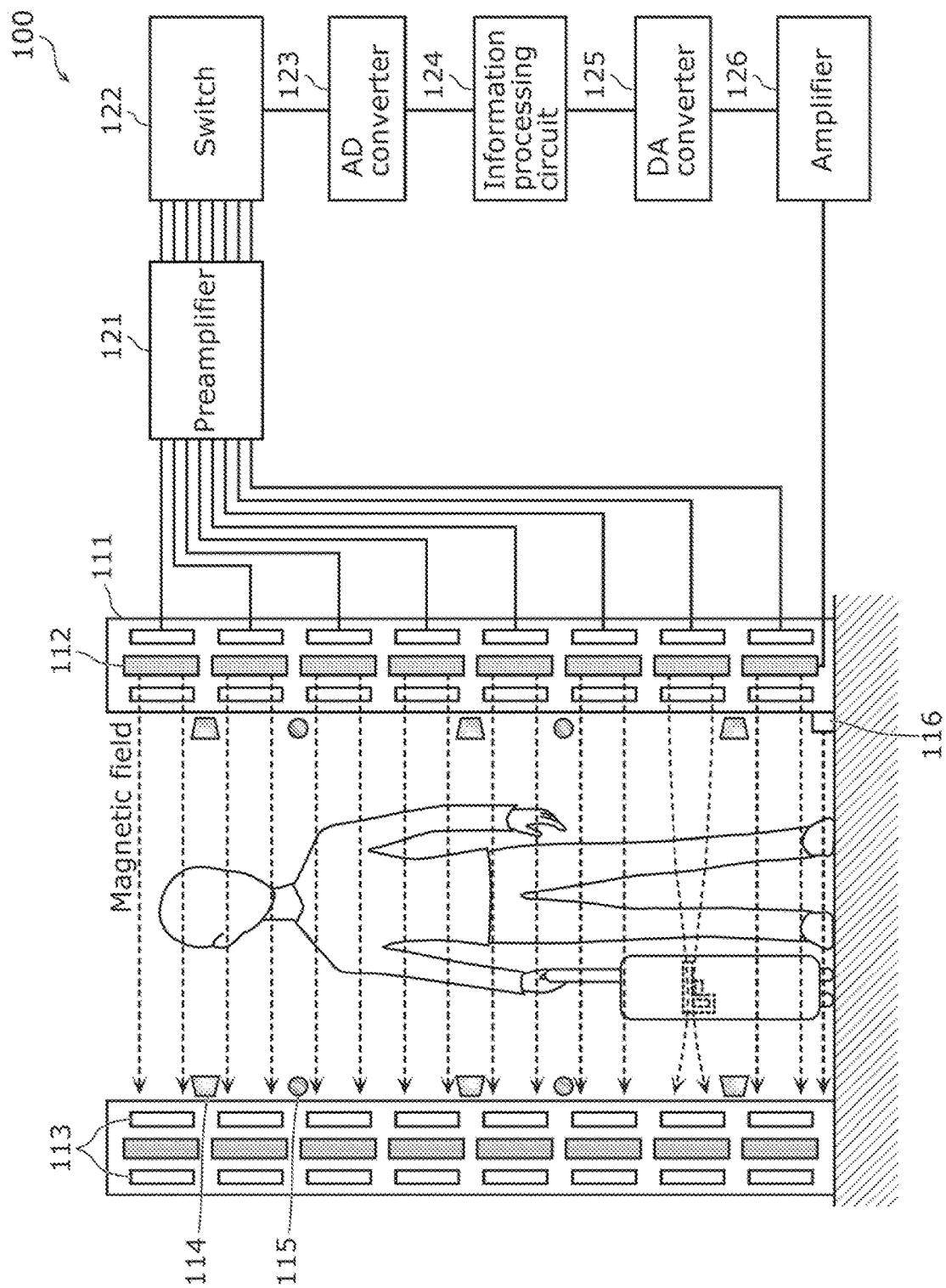
FIG. 1 is a schematic diagram illustrating a magnetic response distribution visualization device according to an embodiment of the present disclosure.

Currently, security checks are conducted at airports and other locations using millimeter wave technology. Because X-rays cannot be used due to the radiation exposure, the usage of electromagnetic waves with lower energy to permeate through, for example, clothing, is being considered.

According to the police, blades and other weapons are hidden not only behind clothing, but also in living bodies and deep inside bags or other objects. Detection of weapons is difficult with millimeter wave technology due to the large number of obstructions, including bags. Walk-through security inspection devices are available, but in practice, due to signal-to-noise ratio problems, the person to be inspected must be nearly stationary. In addition, there are many problems with the current security image inspection technology, such as the inability to detect the inside of a bag if it is concealed under a person's arm, etc., and the need for a separate X-ray inspection of the bag when the inside of the bag cannot be detected.

In order to find a weapon in a bag, such as a metal suitcase, from a physics standpoint, taking permeability into account, high energy rays, or the exact opposite, a static magnetic field, can be used. From the viewpoint of radiation exposure, it is desirable to use a static magnetic field. However, the magnetic field generated by the weapon is spatially spread out, making it difficult to obtain a clear image.

In view of this, for example, a magnetic response distribution visualization device according to one aspect of the present disclosure includes: an induction circuit that induces, from outside a moving object, a magnetic field component that is a component of a magnetic field that satisfies a fundamental equation for magnetic fields; a sensor that senses a strength and a phase of the magnetic field including the magnetic field component altered by the moving object, at a plurality of points in time outside the moving object; and an information processing circuit that, based on a sensing result of the strength and the phase of the magnetic field, a moving speed of the moving object, and the fundamental equation for magnetic fields, calculates a strength and a phase of the magnetic field at a vicinal position closer to the moving object than the sensor, and generates, based on a calculation result of the strength and the phase of the magnetic field, a magnetic response distribution image that shows a distribution of a response of the moving object to the magnetic field component induced by the induction circuit and is used for security inspection.

With this, the magnetic response distribution visualization device can appropriately calculate the strength and the phase of the magnetic field in the vicinity of the moving object based on: positions of the sensor defined relatively at a plurality of points in time based on the moving speed; the sensing result of the strength and the phase of the magnetic field; and the fundamental equation for magnetic fields. The magnetic response distribution visualization device can generate a magnetic response distribution image with high accuracy based on the calculation result of the strength and phase of the magnetic field.

Stated differently, the magnetic response distribution visualization device can generate an image showing the distribution of the response of the moving object to an external field with high accuracy as an image to be used for security inspection.

For example, the information processing circuit: identifies, at each of the plurality of points in time, a sensing position defined as a position of the sensor relative to the moving object, based on the moving speed, to identify a plurality of sensing positions of the sensor relative to the moving object at the plurality of points in time; and calculates the strength and the phase of the magnetic field at the vicinal position by using temporal changes in the sensing result over the plurality of points in time as spatial changes in the sensing result across the plurality of sensing positions.

This enables the magnetic response distribution visualization device to use temporal changes in sensing results as spatial changes. The magnetic response distribution visualization device can therefore appropriately calculate a spatial distribution and can appropriately calculate the strength and the phase of the magnetic field at a vicinal position near the moving object.

For example, the information processing circuit determines whether the moving object includes a detection target object based on the magnetic response distribution image, and when the moving object is determined to include the detection target object, outputs information indicating a location of the detection target object or a location of the moving object to an external terminal.

This enables the magnetic response distribution visualization device to notify of the location of a specific detection target object or the location of the moving object including a specific detection target object.

For example, the magnetic response distribution visualization device further includes an instrument that measures the moving speed.

This enables the magnetic response distribution visualization device to appropriately obtain the moving speed of the moving object.

For example, the magnetic field component induced by the induction circuit is a periodically varying magnetic field component, and the information processing circuit detects, from the sensing result, a magnetic field component having a same frequency as a frequency of the periodically varying magnetic field component, and calculates the strength and the phase of the magnetic field at the vicinal position based on the detected magnetic field component, the moving speed, and the fundamental equation for magnetic fields.

This enables the magnetic response distribution visualization device to appropriately obtain the response to the magnetic field component induced by the induction circuit. Stated differently, the magnetic response distribution visualization device can inhibit noise. The magnetic response distribution visualization device can therefore generate a magnetic response distribution image with high accuracy.

For example, the magnetic field component induced by the induction circuit comprises a first magnetic field component that has a first frequency and penetrates a shielding in the moving object and a second magnetic field component that has a second frequency higher than the first frequency and is shielded by the shielding in the moving object, and the information processing circuit generates the magnetic response distribution image by generating a first image showing a distribution of a response of the moving object to the first magnetic field component induced by the induction circuit and a second image showing a distribution of a response of the moving object to the second magnetic field component induced by the induction circuit, and combining the first image and the second image.

This enables the magnetic response distribution visualization device to generate, as a magnetic response distribution image, a composite image of two images obtained for magnetic field components having two different frequencies. This composite image can both show what is behind the shielding and show the shielding itself. Stated differently, this composite image can properly show the location of an object hidden by the shielding. The magnetic response distribution visualization device can therefore generate a magnetic response distribution image that is effective for security inspection.

For example, the sensor comprises a plurality of sensors disposed on a straight line.

This enables the magnetic response distribution visualization device to sense the strength and the phase of the magnetic field using a one-dimensional sensor array. This makes it possible to reduce the space required for providing the sensors.

For example, the sensor comprises a plurality of sensors disposed on a first straight line and a plurality of sensors disposed on a second straight line that is parallel to the first straight line and farther from the moving object than the first line is.

This enables the magnetic response distribution visualization device to sense the strength and the phase of the magnetic field using two one-dimensional sensor arrays, and sense the strength and the phase of the magnetic field at sensing positions at different distances from the moving object.

For example, the induction circuit comprises a plurality of induction circuits disposed on a straight line.

This enables the magnetic response distribution visualization device to induce a magnetic field component using a one-dimensional induction circuit array. This makes it possible to reduce the space required for providing the induction circuits.

For example, the sensor comprises a plurality of sensors disposed on a plane.

This enables the magnetic response distribution visualization device to sense the strength and the phase of the magnetic field using a two-dimensional sensor array. This enables the magnetic response distribution visualization device to obtain a two-dimensional sensing result at a single point in time. The magnetic response distribution visualization device can therefore combine two-dimensional sensing results obtained at a plurality of points in time to eliminate noise.

For example, the sensor comprises a plurality of sensors disposed on a first plane and a plurality of sensors disposed on a second plane that is parallel to the first plane and farther from the moving object than the first plane is.

This enables the magnetic response distribution visualization device to sense the strength and the phase of the magnetic field using two two-dimensional sensor arrays, and sense the strength and the phase of the magnetic field at sensing positions at different distances from the moving object.

For example, the induction circuit comprises a plurality of induction circuits disposed on a plane.

This enables the magnetic response distribution visualization device to uniformly induce a magnetic field component using a two-dimensional induction circuit array.

For example, the induction circuit and the sensor are disposed on opposite sides of a path of travel of the moving object.

This enables the magnetic response distribution visualization device to sense the strength and the phase of the magnetic field at the sensor which is located on the opposite side of the moving object relative to the induction circuit. With this, when sensing the strength and phase of the magnetic field using the sensor, the magnetic response distribution visualization device can inhibit the influence of direct magnetic field components induced by the induction circuit that have not been affected by the moving object, such as magnetic field components of an environmental magnetic field.

For example, the induction circuit and the sensor are disposed on a same side of a path of travel of the moving object and not on opposite sides of the path of travel.

This enables the magnetic response distribution visualization device to sense the strength and the phase of the magnetic field at the sensor which is located on the same side of the moving object relative to the induction circuit. The space required for providing the induction circuit and the sensor can therefore be reduced.

For example, the induction circuit comprises a plurality of induction circuits disposed on first and second opposite sides of a path of travel of the moving object, the sensor comprises a plurality of sensors disposed on the first side and the second side, and the information processing circuit switches between a first operation in which one or more of the plurality of induction circuits disposed on the first side induce the magnetic field component and one or more of the plurality of sensors disposed on the second side sense the strength and the phase of the magnetic field, and a second operation in which one or more of the plurality of induction circuits disposed on the second side induce the magnetic field component and one or more of the plurality of sensors disposed on the first side sense the strength and the phase of the magnetic field.

This enables the magnetic response distribution visualization device to sense the strength and the phase of the magnetic field using time division on both sides, making it possible to obtain a lot of information.

For example, the information processing circuit selects, as the magnetic response distribution image, either a first magnetic response distribution image generated based on the first operation or a second magnetic response distribution image generated based on the second operation.

This enables the magnetic response distribution visualization device to adaptively use one of the two magnetic response distribution images corresponding to both sides.

For example, a security inspection system according to one aspect of the present disclosure includes: the magnetic response distribution visualization device described above; and a thermographic device for performing diagnostic imaging on a person corresponding to the moving object.

This enables the security inspection system to generate an image showing the distribution of the response of a moving object to an external field with high accuracy as an image to be used for security inspection, and to perform diagnostic imaging on a person who may be carrying a virus.

For example, a magnetic response distribution visualization method according to one aspect of the present disclosure includes: inducing, from outside a moving object, a magnetic field component that is a component of a magnetic field that satisfies a fundamental equation for magnetic fields, using an induction circuit; sensing, using a sensor, a strength and a phase of the magnetic field including the magnetic field component altered by the moving object, at a plurality of points in time outside the moving object; and based on a sensing result of the strength and the phase of the magnetic field, a moving speed of the moving object, and the fundamental equation for magnetic fields, calculating a strength and a phase of the magnetic field at a vicinal position closer to the moving object than the sensor, and generating, based on a calculation result of the strength and the phase of the magnetic field, a magnetic response distribution image that shows a distribution of a response of the moving object to the magnetic field component induced by the induction circuit and is used for security inspection.

With this, it is possible to appropriately calculate the strength and the phase of the magnetic field in the vicinity of the moving object based on: positions of the sensor defined relatively at a plurality of points in time based on the moving speed; the sensing result of the strength and the phase of the magnetic field; and the fundamental equation for magnetic fields. The magnetic response distribution visualization device can generate a magnetic response distribution image with high accuracy based on the calculation result of the strength and phase of the magnetic field.

Stated differently, the magnetic response distribution visualization device can generate an image showing the distribution of the response of the moving object to an external field with high accuracy as an image to be used for security inspection.

Hereinafter, embodiments will be described with reference to the drawings. Each of the following embodiments describes a general or specific example. The numerical values, shapes, materials, elements, the arrangement and connection of the elements, steps, the order of the steps etc., presented in the following embodiments are mere examples, and do not limit the scope of the claims.

Hereinafter, mainly a magnetic response distribution visualization device that uses the magnetic field will be described as one example of a magnetic response distribution visualization device. The magnetic field components described below are the components that make up the magnetic field. The magnetic field components may be each of several magnetic fields superimposed on the overall magnetic field.

Embodiment

FIG. 1 is a schematic diagram illustrating a magnetic response distribution visualization device according to the present embodiment. Magnetic response distribution visualization device 100 illustrated in FIG. 1 includes, for example, induction circuit 112, magnetic sensor 113, camera 114, infrared sensor 115, laser device 116, preamplifier 121, switch 122, AD converter 123, information processing circuit 124, DA converter 125, and amplifier 126.

Magnetic response distribution visualization device 100 does not need to include each of camera 114, infrared sensor 115, and laser device 116; magnetic response distribution visualization device 100 may include only one of camera 114, infrared sensor 115, and laser device 116. Magnetic response distribution visualization device 100 may include a plurality of induction circuits 112, a plurality of magnetic sensors 113, a plurality of cameras 114, a plurality of infrared sensors 115, and a plurality of laser devices 116.

In the example in FIG. 1, a plurality of induction circuits 112 and a plurality of magnetic sensors 113 are included internally in security gate 111. More specifically, a plurality of sets, each including one induction circuit 112 and two magnetic sensors 113 disposed on either side of the one induction circuit 112, are arranged in the height direction, i.e., vertically.

Magnetic response distribution visualization device 100 generates an image showing the magnetic response distribution of a moving object passing through security gate 111. This image can show the strength and phase of the magnetic field. This image can show magnetic material, more specifically ferromagnetic material, contained in the moving object. Examples of moving objects include a person and luggage held by a person. The image generated by magnetic response distribution visualization device 100 can therefore show a weapon or other object concealed by a person.

Although not illustrated in FIG. 1, camera 114, infrared sensor 115, and laser device 116 are connected to information processing circuit 124. All magnetic sensors 113 are connected to preamplifier 121. All induction circuits 112 are connected to amplifier 126.

Induction circuit 112 is an electrical circuit that induces a magnetic field component. Induction circuit 112 is, for example, a coil that induces a magnetic field component of a few millitesla or less. Induction circuit 112 may be a conductive wire or printed circuit board wiring, for example. For example, an alternating current is applied to induction circuit 112 by information processing circuit 124 via DA converter 125 and amplifier 126. This induces a magnetic field component of the alternating current. The magnetic field component induced by induction circuit 112 changes by the moving object.

The above-described alternating current is a low-frequency alternating current of 100 kHz or less. The magnetic field component of the alternating current described above is therefore a slowly varying magnetic field component. In such cases, when a high-frequency alternating current is used, the generation of an eddy current makes it difficult to identify changes in the magnetic field component in, for example, an object in a highly conductive metal case. On the other hand, if a direct current is used, it is difficult to eliminate noise. A low-frequency alternating current is therefore used.

In the example in FIG. 1, a plurality of induction circuits 112 are arranged vertically in one dimension on the right and left sides of security gate 111.

Magnetic sensor 113 is a sensor that senses magnetism. Magnetic sensor 113 may be, for example, a tunneling magneto resistive (TMR) element, a giant magneto resistive (GMR) element, a superconducting quantum interference device (SQUID) element, or a magneto-impedance (MI) element.

More specifically, magnetic sensor 113 senses magnetism in a magnetic field that includes a magnetic field component altered by a moving object. For example, magnetic sensor 113 senses magnetism with nanotesla or picotesla accuracy. Magnetic sensor 113 outputs a magnetic sensor signal as a sensing result. As used herein, the term "sense" can also be expressed as "measure".

In the example in FIG. 1, the plurality of magnetic sensors 113 are aligned vertically on the right and left sides of security gate 111. Furthermore, on each side of security gate 111, the plurality of magnetic sensors 113 are arranged along a straight line closer to the inner side of security gate 111 and along a straight line farther from the inner side of security gate 111.

Camera 114 is an imaging device that captures images of the subject. More specifically, camera 114 captures images of a moving object passing through security gate 111. Camera 114 may be a motion camera that measures the moving speed of a moving object passing through security gate 111.

Infrared sensor 115 is a sensor that senses infrared light. Infrared sensor 115 senses infrared light emitted from or reflected by a moving object passing through security gate 111.

Laser device 116 is a device that emits laser light. Laser device 116 is, for example, a semiconductor laser. More specifically, laser device 116 emits laser light and receives the laser light reflected from a moving object passing through security gate 111 to sense the moving object. The distance to the moving object may be obtained according to the sensing result of the moving object.

A configuration in which each of a plurality of laser devices 116 disposed spaced apart from each other sense a moving object is also acceptable. The moving speed may then be obtained according to the sensing results of the moving object by the plurality of laser device 116.

Preamplifier 121 is a circuit that amplifies minute signals. This provides signals that can be used in later-stage circuits (such as AD converter 123 and information processing circuit 124). For example, preamplifier 121 amplifies the magnetic sensor signal output from magnetic sensor 113 and outputs the amplified magnetic sensor signal. Preamplifier 121 may be provided for each of the plurality of magnetic sensors 113.

Switch 122 is a circuit for switching electrical pathways. More specifically, switch 122 sequentially inputs the magnetic sensor signals obtained from the plurality of magnetic sensors 113 via preamplifier 121 to AD converter 123.

AD converter 123 is a digital-to-analog converter for converting an analog signal to a digital signal. AD converter 123 obtains the magnetic sensor signal input from magnetic sensor 113 via preamplifier 121 and switch 122 as an analog signal and converts the magnetic sensor signal obtained as an analog signal into a digital signal. AD converter 123 then inputs the magnetic sensor signal converted into a digital signal to information processing circuit 124.

Information processing circuit 124 is an electrical circuit that performs information processing. Information processing circuit 124 may be a computer or a processor of a computer, for example.

More specifically, information processing circuit 124 obtains the magnetic sensor signal as a sensing result of the magnetism. Information processing circuit 124 obtains the moving speed of the moving object based on information obtained from camera 114, infrared sensor 115, laser device 116, or a combination thereof.

Information processing circuit 124 then calculates the strength and phase of the magnetic field at a vicinal position near the moving object based on the sensing result of the magnetism, the moving speed of the moving object, and the Laplace equation, which is a fundamental equation that the field (specifically, the static magnetic field) satisfies. Stated differently, information processing circuit 124 reconstructs the strength and phase of the magnetic field.

Information processing circuit 124 then generates an image showing the magnetic response distribution of the moving object based on the calculated strength and phase of the magnetic field. Information processing circuit 124 may display the image on a display by outputting the image to the display. Alternatively, information processing circuit 124 may print the image via a printer by outputting the image to the printer. Alternatively, information processing circuit 124 may transmit the image as electronic data to another device via wired or wireless communication.

Information processing circuit 124 inputs a control signal to DA converter 125. This input applies a current to induction circuit 112 via DA converter 125 and amplifier 126. For example, information processing circuit 124 applies an alternating current to induction circuit 112 via DA converter 125 and amplifier 126.

DA converter 125 is a converter for converting a digital signal to an analog signal. More specifically, DA converter 125 obtains the control signal input from information processing circuit 124 as a digital signal and converts the control signal obtained as a digital signal into an analog signal. DA converter 125 then inputs the control signal converted into an analog signal to amplifier 126.

Amplifier 126 applies a current corresponding to the control signal converted into an analog signal to induction circuit 112. For example, amplifier 126 applies an alternating current to induction circuit 112.

For example, the magnetic field component is induced by induction circuits 112 on the right side of security gate 111. The magnetic field component induced by induction circuits 112 on the right side changes by the moving object. In particular, the magnetic field component changes greatly by the magnetic material-more specifically, the ferromagnetic material-contained in the moving object. The magnetism in the magnetic field including the changed magnetic field component is then sensed by magnetic sensors 113 on the left side of security gate 111.

The operations performed on the left and right sides are switched so as to be performed alternately by, for example, a switch, which is not shown in the figure. Stated differently, the operation in which the magnetic field component is induced from the right side and magnetism is sensed on the left side, and the operation in which the magnetic field component is induced from the left side and magnetism is sensed on the right side are switched so as to be performed alternately.

Information processing circuit 124 then calculates the strength and phase of the magnetic field at a vicinal position near the moving object by using the sensing results from the left and right sides as Neumann and Dirichlet boundary conditions. Information processing circuit 124 then generates an image showing the magnetic response distribution of the moving object based on the calculation result.

FIG. 1 is a schematic diagram. The number and size of the plurality of induction circuits 112 and the number and size of the plurality of magnetic sensors 113 may be different from the example in FIG. 1. A larger number of smaller induction circuits 112 may be arranged in higher density, and a larger number of smaller magnetic sensors 113 may be arranged in higher density. The same applies to the other schematic diagrams as well.

Each of camera 114, infrared sensor 115, and laser device 116 may also serve as an instrument that measures the moving speed of a moving object passing through security gate 111.

Figure 2:
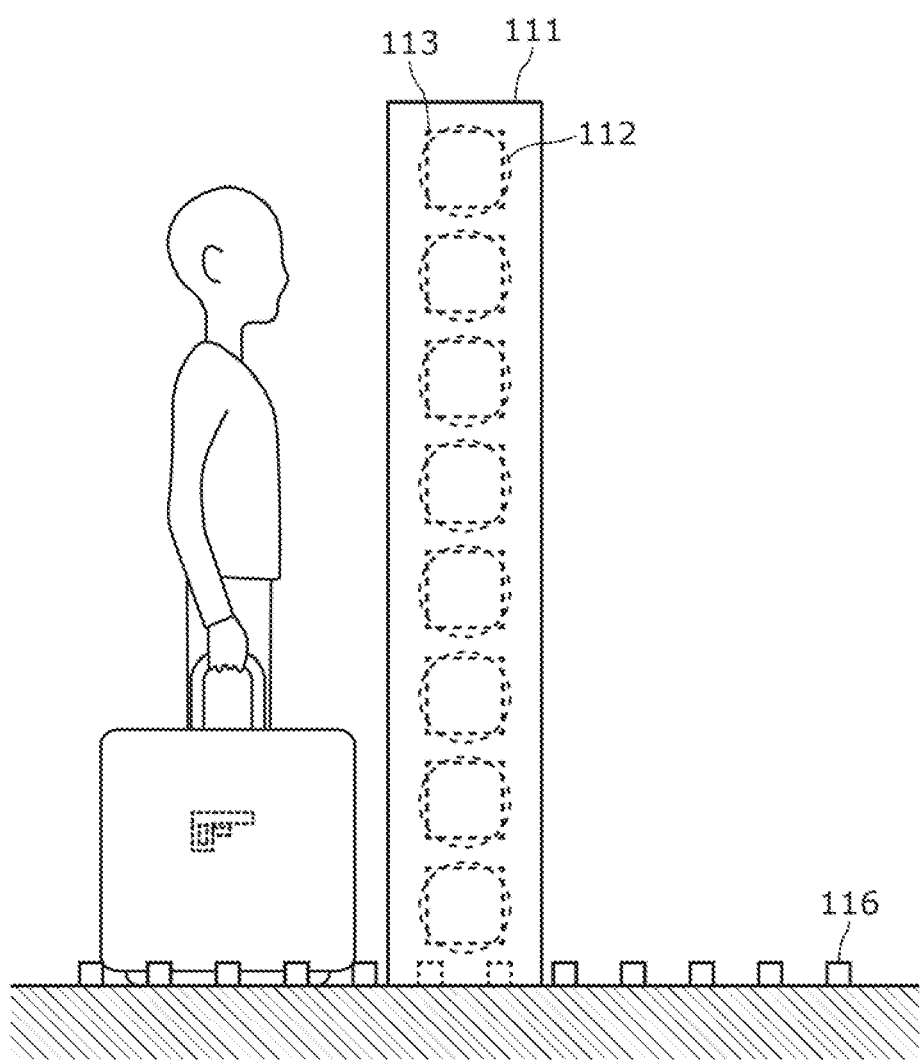
FIG. 2 is a schematic diagram illustrating a side surface of a security gate according to an embodiment of the present disclosure.

FIG. 2 is a schematic diagram illustrating a side surface of security gate 111 illustrated in FIG. 1. The plurality of induction circuits 112 and the plurality of magnetic sensors 113 are aligned perpendicular to the direction of travel of the moving object.

The plurality of induction circuits 112, which are arranged in one dimension perpendicular to the direction of travel of the moving object, can scan in one dimension in the direction opposite to the direction of travel of the moving object, relative to the moving object, as a result of the moving object passing through security gate 111. At the same time, the plurality of magnetic sensors 113, which are arranged in one dimension perpendicular to the direction of travel of the moving object, can scan in one dimension in the direction opposite to the direction of travel of the moving object, relative to the moving object, as a result of the moving object passing through security gate 111.

This allows the plurality of magnetic sensors 113 to scan along a plane that is relative to the moving object and parallel to the direction of travel of the moving object. The magnetic field component is induced by induction circuits 112 on the opposite side of the moving object relative to the plurality of magnetic sensors 113 that sense the magnetism at this time. The magnetism of the magnetic field, including the magnetic field component altered by the moving object, is then sensed by the plurality of magnetic sensors 113. With this, a sensing result of the magnetism on such a plane can be obtained.

Magnetic response distribution visualization device 100 can also obtain the moving speed of the moving object. Magnetic response distribution visualization device 100 can then identify the position of each magnetic sensor 113 relative to the moving object at multiple points in time based on the moving speed of the moving object. Stated differently, magnetic response distribution visualization device 100 can identify information at each position at which a sensing result is obtained, and can appropriately reconstruct the strength and phase of the magnetic field based on the sensing results at the identified positions.

As illustrated in FIG. 1, there are a plurality of magnetic sensors 113 that are relatively close to the moving object and a plurality of magnetic sensors 113 that are relatively far from the moving object. With this, a sensing result of the magnetism can be obtained on two planes.

Figure 3:
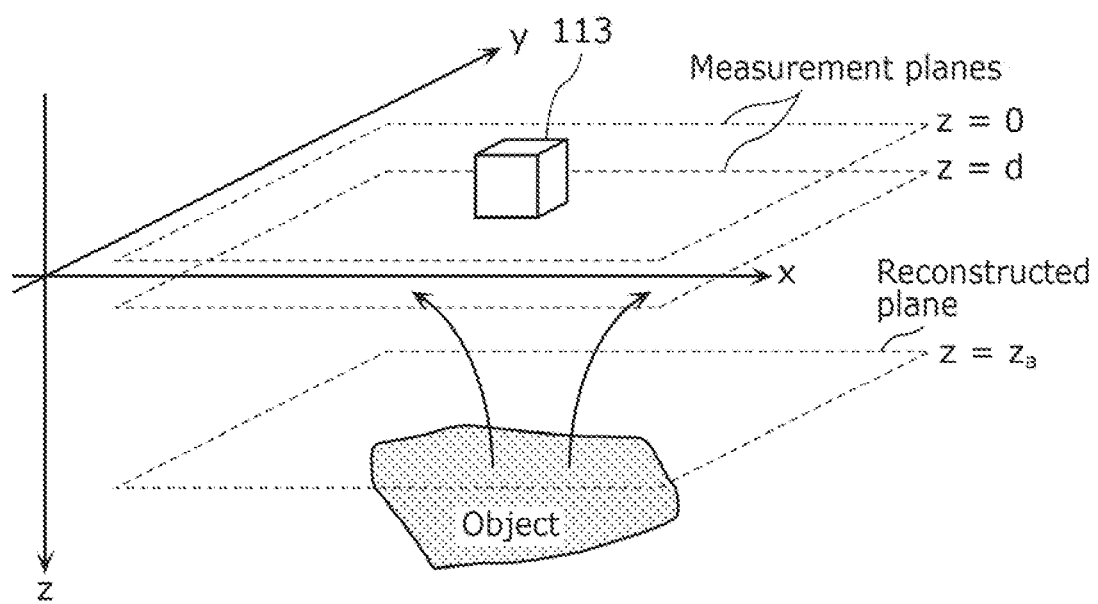
FIG. 3 is an illustration of a reconstruction process according to an embodiment of the present disclosure.

FIG. 3 is an illustration of the reconstruction process performed by information processing circuit 124 illustrated in FIG. 1. The two measurement planes illustrated in FIG. 3 represent the two planes from which the sensing results of the magnetism are obtained. Although omitted in FIG. 3, the object is magnetized by the magnetic field component induced from induction circuit 112. Magnetic sensor 113 senses the magnetism of the magnetic field including the magnetic field component induced from the magnetized object.

For example, the fundamental equation for a field in free space absent of a magnetic source is expressed by the Laplace equation. More specifically, the following equation (1) holds true for $H_z(x, y, z)$, which is the z-component of the magnetic field vector in the xyz Cartesian coordinate system.

[Math. 1]

$$\Delta H_z = 0 \tag{1}$$

The general solution of equation (1) is expressed as shown in equation (2) below.

[Math. 2]

$$H_z(x, y, z) = \frac{1}{(2\pi)^2} \int\int e^{ik_x x + ik_y y} \left\{ a(k_x, k_y) e^{z\sqrt{k_x^2 + k_y^2}} + b(k_x, k_y) e^{-z\sqrt{k_x^2 + k_y^2}} \right\} dk_x dk_y \tag{2}$$

In equation (2) above, $k_x$ and $k_y$ represent the wavenumbers in the x- and y-directions, respectively. Also, $a(k_x, k_y)$ and $b(k_x, k_y)$ are functions expressed in terms of $k_x$ and $k_y$. For example, the measurement yields the z-component $H_z(x, y, 0)$ of the magnetic field vector in the plane of z=0, and the z-direction gradient $\partial/\partial z H_z(x, y, z)|_{z=0}$ of the z-component of the magnetic field vector. Using these, $a(k_x, k_y)$ and $b(k_x, k_y)$ in equation (2) can be obtained as illustrated in equations (3) and (4) below, respectively.

[Math. 3]

$$a(k_x, k_y) = \frac{1}{2}\left[f(k_x, k_y) + \frac{g(k_x, k_y)}{\sqrt{k_x^2 + k_y^2}}\right] \tag{3}$$

[Math. 4]

$$b(k_x, k_y) = \frac{1}{2}\left[f(k_x, k_y) - \frac{g(k_x, k_y)}{\sqrt{k_x^2 + k_y^2}}\right] \tag{4}$$

In equations (3) and (4), $f(k_x, k_y)$ is the two-dimensional Fourier transform image of $H_z(x, y, 0)$, and $g(k_x, k_y)$ is the two-dimensional Fourier transform image of $\partial/\partial z H_z(x, y, z)|_{z=0}$. By substituting equations (3) and (4) into equation (2), $H_z$ can be obtained as illustrated in equation (5) below.

[Math. 5]

$$H_z(x, y, z) = \frac{1}{(2\pi)^2} \int\int e^{ik_x x + ik_y y} \left\{ \frac{1}{2}\left(f(k_x, k_y) + \frac{g(k_x, k_y)}{\sqrt{k_x^2 + k_y^2}}\right) e^{z\sqrt{k_x^2 + k_y^2}} + \frac{1}{2}\left(f(k_x, k_y) - \frac{g(k_x, k_y)}{\sqrt{k_x^2 + k_y^2}}\right) e^{-z\sqrt{k_x^2 + k_y^2}} \right\} dk_x dk_y \tag{5}$$

With the above method, it is possible to obtain $H_z(x, y, z)$ at any z-coordinate in space absent of a magnetic source using $H_z(x, y, 0)$, which is the Dirichlet boundary condition, and $\partial/\partial z H_z(x, y, z)|_{z=0}$, which is the Neumann boundary condition. This means that the magnetic field at a reconstructed plane close to the object can be reconstructed from the magnetic field at the measurement plane, which is the xy plane at z=0, and a measurement plane in the vicinity thereof.

More specifically, $H_z(x, y, 0)$ is obtained as the sensing result at the measurement plane at z=0. $\partial/\partial z H_z(x, y, z)|_{z=0}$ is calculated based on the sensing results at the two measurement planes. For example, a sensing result at the measurement plane at z=0 and a sensing result at the measurement plane at z=d are obtained. $\partial/\partial z H_z(x, y, z)|_{z=0}$ can then be approximated by dividing the difference between the sensing result at the measurement plane at z=0 and the sensing result at the measurement plane at z=d by d, which is the distance between these two measurement planes.

Then, $f(k_x, k_y)$ and $g(k_x, k_y)$ are obtained by performing a two-dimensional Fourier transform with respect to x and y on $H_z(x, y, 0)$ and $\partial/\partial z H_z(x, y, z)|_{z=0}$ obtained from the sensing results. Then, by substituting $f(k_x, k_y)$ and $g(k_x, k_y)$ obtained by the two-dimensional Fourier transform into equation (5), $H_z(x, y, z)$ at any z-coordinate in space absent of a magnetic source is obtained. This makes it possible to accurately obtain information on the magnetic field in the reconstructed plane.

Here, the measurement data corresponding to the sensing results is a two-dimensional data matrix of the z-components of the magnetic field vector as elements. However, the reconstruction can be performed in the same way even if the data matrix is a two-dimensional data matrix including higher-order differentials of the z-components of the magnetic field vector in the z-direction as elements.

Note that $H_z(x, y, 0)$ obtained as a sensing result corresponds to the strength and phase of the magnetic field at the position $(x, y, 0)$. Similarly, $H_z(x, y, z)$ obtained as a calculation result corresponds to the strength and phase of the magnetic field at the position $(x, y, z)$.

Figure 4:
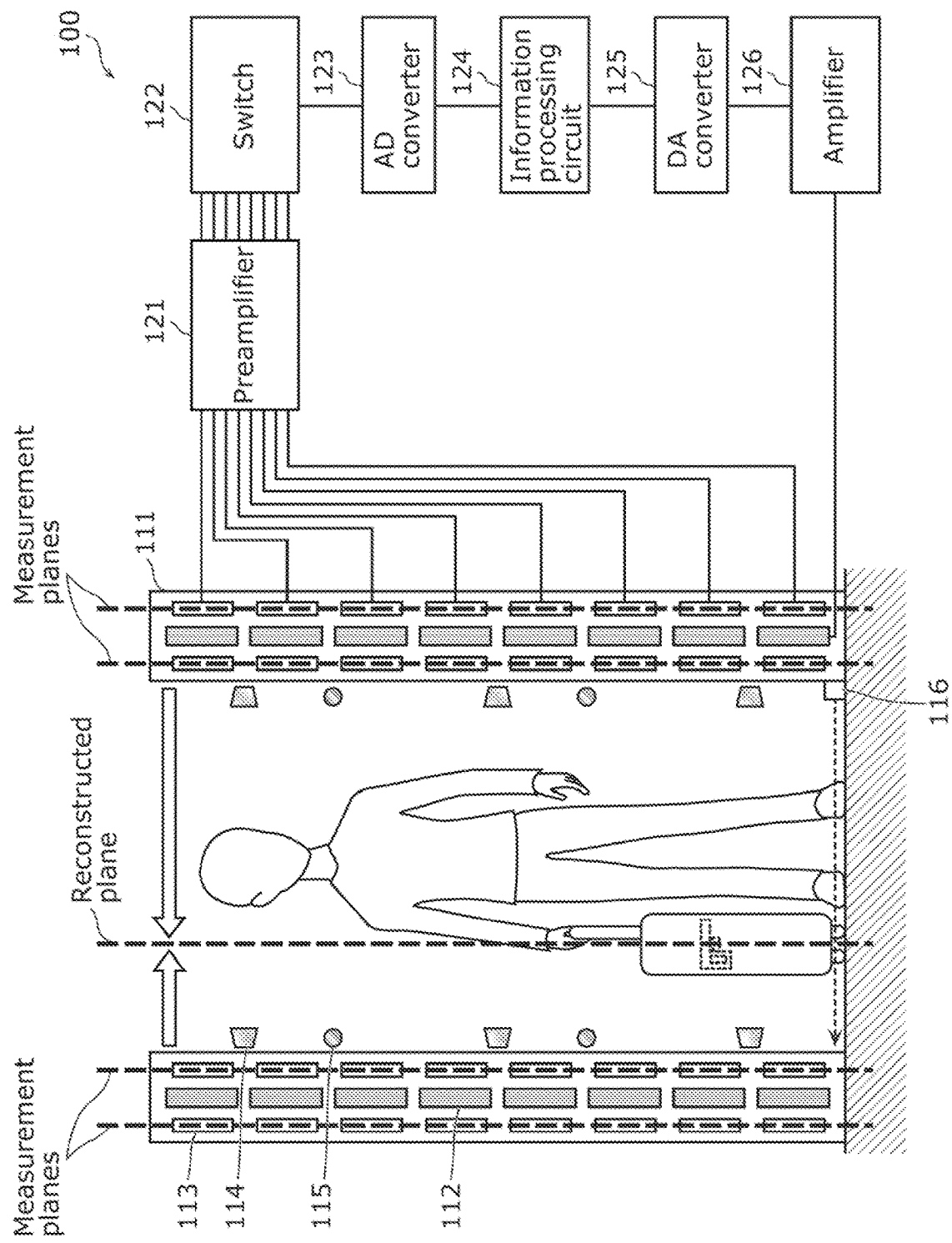
FIG. 4 is a schematic diagram illustrating measurement planes and a reconstructed plane according to an embodiment of the present disclosure.

FIG. 4 is a schematic diagram illustrating the measurement planes and the reconstructed plane illustrated in FIG. 3 in magnetic response distribution visualization device 100 illustrated in FIG. 1.

Magnetic response distribution visualization device 100 can generate an image showing the magnetic field in the reconstructed plane based on the sensing results in the two measurement planes corresponding to the two columns of magnetic sensors 113 on the left side, which shows the magnetic response distribution of the moving object. Similarly, magnetic response distribution visualization device 100 can generate an image showing the magnetic field in the reconstructed plane based on the sensing results in the two measurement planes corresponding to the two columns of magnetic sensors 113 on the right side, which shows the magnetic response distribution of the moving object.

Information processing circuit 124 of magnetic response distribution visualization device 100 may use one image among the image generated based on the left side sensing results and the image generated based on the right side sensing results.

For example, information processing circuit 124 may determine whether the moving object is close to the left side or close to the right side based on information obtained from camera 114, infrared sensor 115, laser device 116, or a combination thereof. If the moving object is close to the left side, the image generated based on the left side sensing results may be used. If the moving object is close to the right side, the image generated based on the right left side sensing results may be used.

Among the image generated based on the left side sensing results and the image generated based on the right side sensing results, the image with a higher contrast may be used.

Information processing circuit 124 may identify the position of the reconstructed plane based on information obtained from camera 114, infrared sensor 115, laser device 116, or a combination thereof. For example, information processing circuit 124 may determine the position of the moving object based on information obtained from camera 114, infrared sensor 115, laser device 116, or a combination thereof. Information processing circuit 124 may then identify the position of the moving object or a position near the position of the moving object as the position of the reconstructed plane.

Alternatively, information processing circuit 124 may generate a plurality of reconstructed images corresponding to a plurality of reconstructed planes and use the reconstructed image with the highest contrast from among the plurality of reconstructed images as the final reconstructed image.

Figure 5:
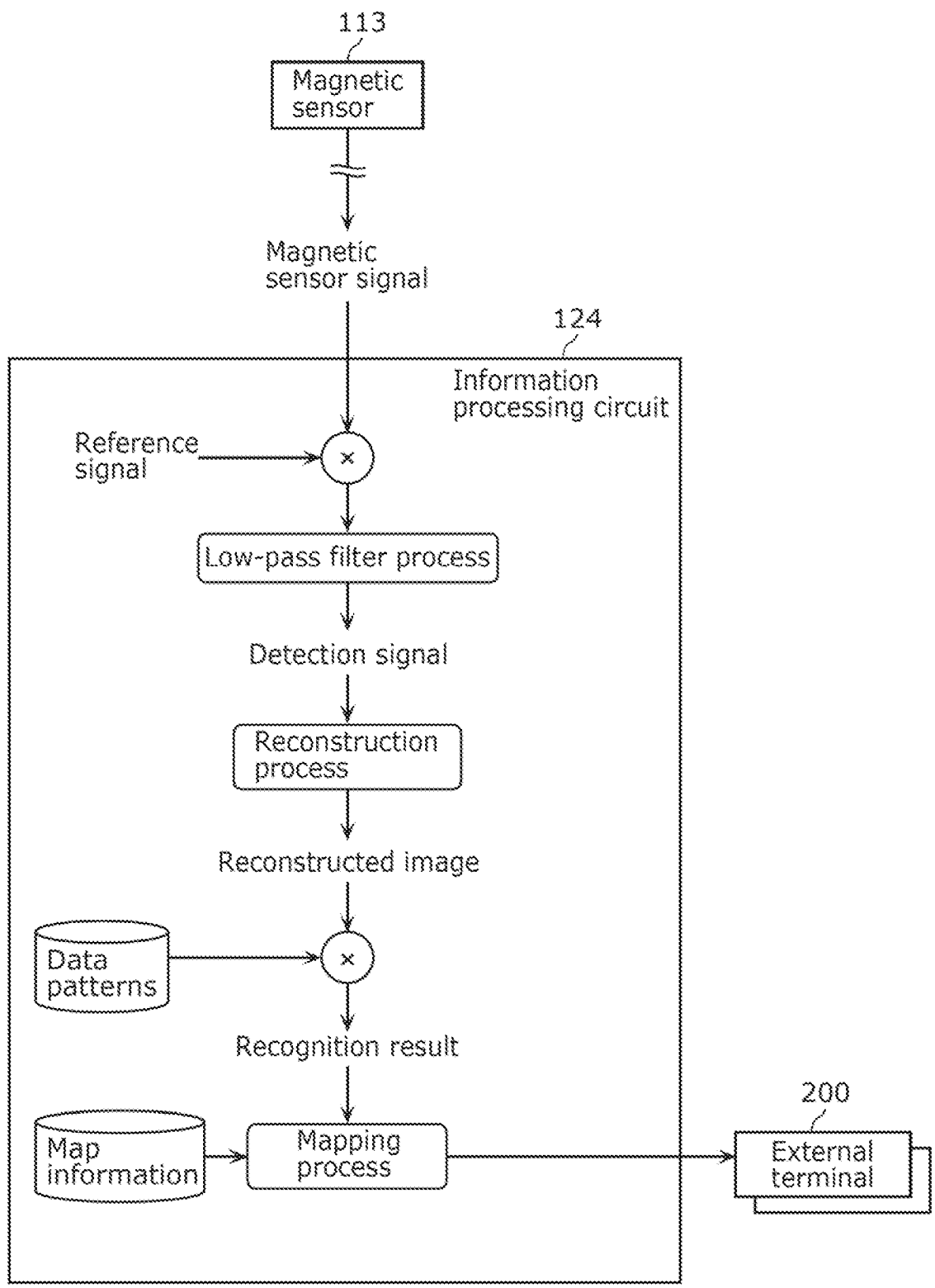
FIG. 5 is a schematic diagram illustrating an information processing circuit according to an embodiment of the present disclosure.

FIG. 5 is a schematic diagram illustrating operations performed by information processing circuit 124 illustrated in FIG. 1. Information processing circuit 124 obtains the magnetic sensor signal from magnetic sensor 113 via, for example, preamplifier 121. Information processing circuit 124 then performs phase detection. More specifically, information processing circuit 124 first multiplies the magnetic sensor signal with a reference signal. The reference signal is an alternating current signal indicating the alternating current applied to induction circuit 112. The direct current component of the multiplication result signal obtained by the multiplication corresponds to the magnetic field component having the same frequency as the frequency of the alternating current applied to induction circuit 112.

Information processing circuit 124 then applies a low-pass filter to the multiplication result signal to block the alternating current component of the multiplication result signal and pass the direct current component of the multiplication result signal. With this, a detection signal corresponding to the magnetic field component having the same frequency as the frequency of the alternating current applied to induction circuit 112 is obtained. This detection signal may be used as the sensing result. Stated differently, the sensing result to which, for example, the processing of preamplifier 121 and phase detection processing have been applied may be used in the reconstruction process.

For example, information processing circuit 124 performs phase detection processing in a digital circuit as digital signal processing on the magnetic sensor signal converted into a digital signal in AD converter 123. Alternatively, information processing circuit 124 may obtain the magnetic sensor signal as an analog signal without passing through AD converter 123. Information processing circuit 124 may then perform phase detection processing on the magnetic sensor signal obtained as an analog signal in an analog circuit as analog signal processing.

Information processing circuit 124 then performs the reconstruction process as described with reference to FIG. 3. This results in a reconstructed image showing the strength and phase of the magnetic field in the reconstructed plane, which shows the magnetic response distribution of the moving object.

Information processing circuit 124 then matches the reconstructed image to a data pattern stored in a database and performs the recognition process for the reconstructed image. Matching the reconstructed image to the data pattern may be done using the multiplication of the reconstructed image and the data pattern.

If a weapon is recognized as a result of the recognition process, information processing circuit 124 maps the coordinates of security gate 111 to the map information stored in the database. For example, information processing circuit 124 generates an image with a pin dropped at the coordinates of security gate 111 on the map, with a risk value written on it. Information processing circuit 124 then transmits the generated image to external terminal 200.

External terminal 200 may be a general-purpose computer device, a monitoring device, a cellular phone, a portable terminal, a smartphone, or a tablet, etc.

For example, the police constantly monitor the coordinates of security gate 111 where a weapon is recognized among a plurality of security gates 111, and take action to seize the dangerous person. Information processing circuit 124 may also determine the route of travel of the dangerous person from a plurality of security gates 111 installed at various locations. In doing so, information related to the cellular phone held by the dangerous person may be collected and used to determine the route of travel. Information on the best evacuation route may then be communicated to the general public within a 1 km perimeter, for example.

Information processing circuit 124 may output information such as the above image showing the coordinates of security gate 111 where the weapon was recognized, the route of travel of the dangerous person, and the best evacuation route to external terminal 200 via wired or wireless communication. Information processing circuit 124 may also obtain images of the dangerous person from camera 114 and output them to external terminal 200.

Information processing circuit 124 may also obtain the moving speed of the dangerous person based on information obtained from camera 114, infrared sensor 115, laser device 116, or a combination thereof, and reflect the moving speed of the dangerous person in the dangerous person's route of travel.

Information processing circuit 124 may detect a person passing through security gate 111 based on information obtained from camera 114, infrared sensor 115, laser device 116, or a combination thereof. Information processing circuit 124 may then perform the operations described above when a person is detected passing through security gate 111.

In the above, induction circuits 112 and magnetic sensors 113 are included in security gate 111, but induction circuits 112 and magnetic sensors 113 may be included in a pole or similar structure for prohibiting vehicle entry.

Magnetic response distribution visualization device 100 according to the present embodiment can properly calculate the strength and phase of the magnetic field in the vicinity of a moving object based on the position of magnetic sensor 113 determined relative to the moving object based on the moving speed, the sensing result of the magnetism, and the fundamental equation for a field. Magnetic response distribution visualization device 100 can then generate an image showing the magnetic response distribution with high accuracy as an image to be used for security inspections, based on the calculation result of the strength and phase of the magnetic field.

The magnetic response of an object typically carried by a person is assumed to be small, while the magnetic response of a weapon is assumed to be large due to its ferromagnetic nature. For example, the magnetic response of aluminum and copper used in electrical products typically carried by a person is small. On the other hand, the magnetic response of iron used in weapons is large. Images showing magnetic response distributions are therefore particularly useful for security inspections.

The distribution of the offender's metal and the distribution of the magnetic field response may be observed separately, for example, by increasing the frequency of the magnetic field applied from induction circuit 112, which is, for example, a coil, and by using the shielding of a metal material such as aluminum. This allows for more precise determination of the weapon.

Figure 6:
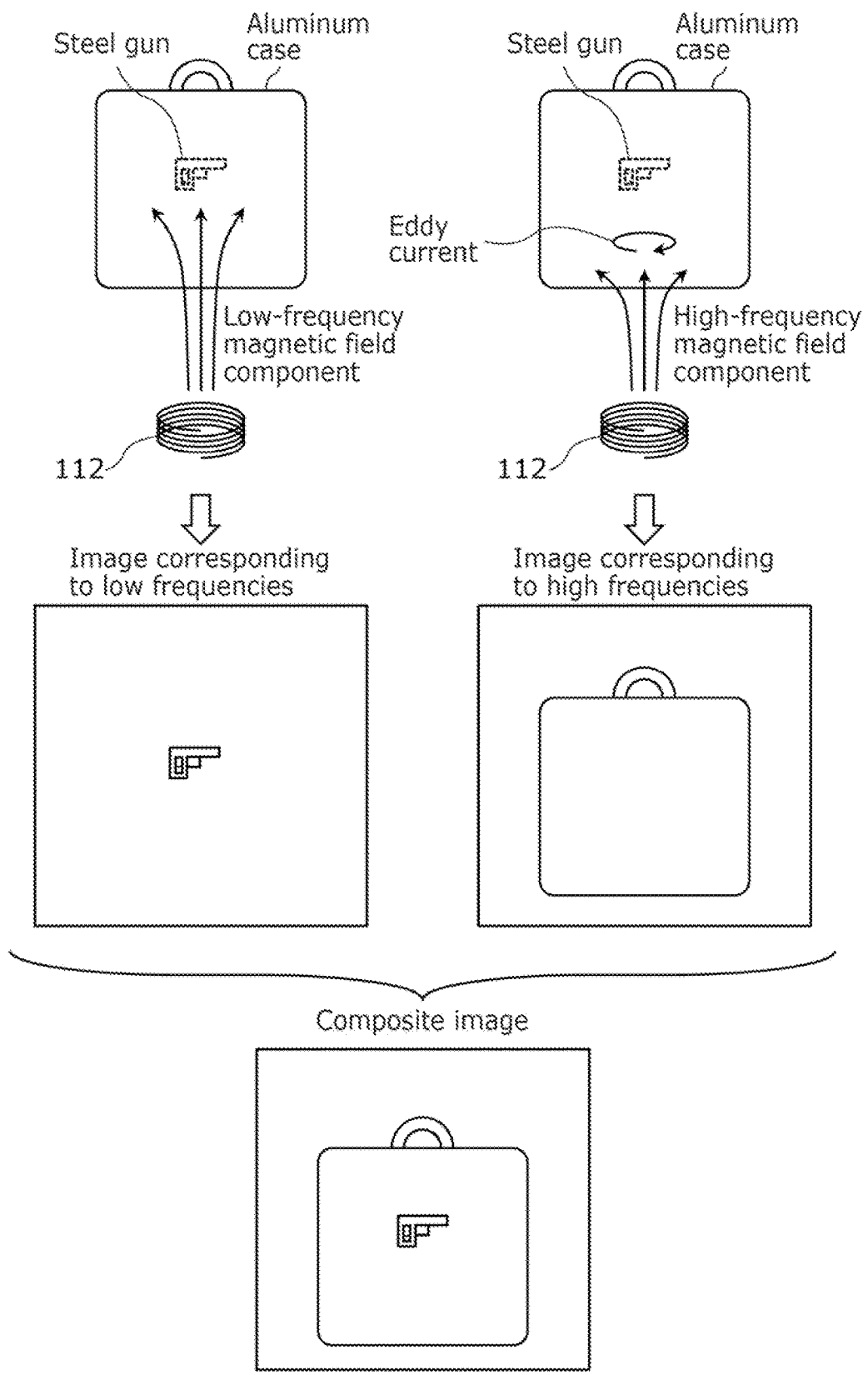
FIG. 6 is a schematic diagram illustrating an example of image compositing according to an embodiment of the present disclosure.

FIG. 6 is a schematic diagram illustrating an example of image compositing according to the present embodiment. In the example in FIG. 6, an iron gun is stored in an aluminum case. First, a low-frequency magnetic field component is induced by induction circuit 112, for example. The low-frequency magnetic field component penetrates the aluminum case. Stated differently, the low-frequency magnetic field component is not shielded by the aluminum case. The image produced for low frequencies therefore shows the iron gun stored in the aluminum case.

Next, a high-frequency magnetic field component is induced by induction circuit 112, for example. The high-frequency magnetic field component induces eddy currents in the aluminum case and does not penetrate the aluminum case. Stated differently, the high-frequency magnetic field component is shielded by the aluminum case. The image produced for high frequencies therefore does not show the iron gun stored in the aluminum case, but rather shows the aluminum case itself.

Information processing circuit 124 may combine the image generated for low frequencies with the image generated for high frequencies. For example, information processing circuit 124 may combine the image generated for low frequencies with the image generated for high frequencies by averaging the two images. The resulting composite image can show both the iron gun stored in the aluminum case and the aluminum case itself. Stated differently, the resulting composite image can clearly show that the iron gun is stored in the aluminum case.

Information processing circuit 124 can therefore generate a composite image that is effective for security inspection.

Induction circuit 112 may induce both low-frequency and high-frequency magnetic field components simultaneously, or induce low-frequency and high-frequency magnetic field components at different times. For each of the low-frequency and high-frequency magnetic field components, magnetic sensor 113 senses the magnetism according to the timing at which the magnetic field component is induced, and information processing circuit 124 generates an image.

Figure 7:
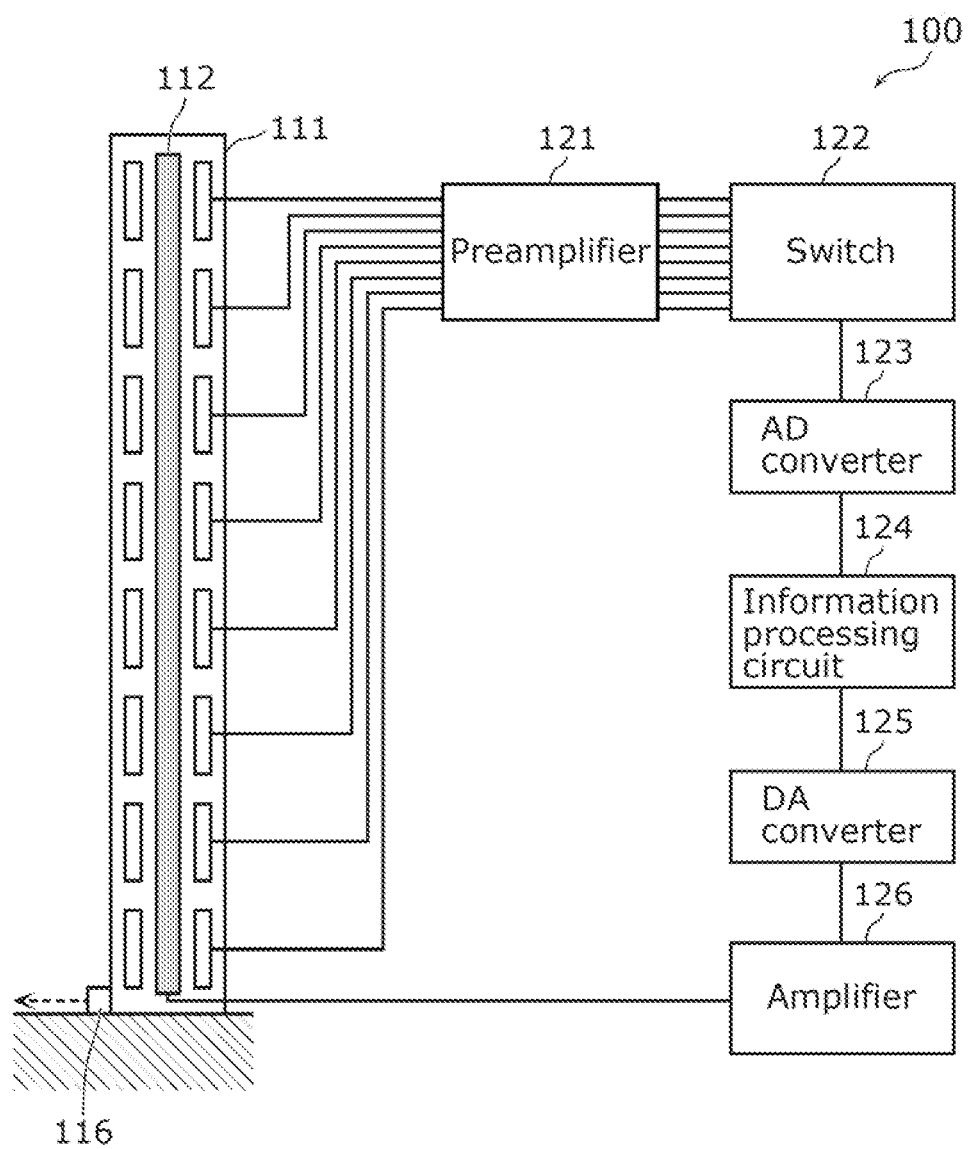
FIG. 7 is a schematic diagram illustrating a variation of an induction circuit according to an embodiment of the present disclosure.

FIG. 7 is a schematic diagram illustrating a variation of induction circuit 112 illustrated in FIG. 1. In the example in FIG. 1, a plurality of induction circuits 112 are located on each side of security gate 111, whereas in the example in FIG. 7, one induction circuit 112 is located on each side.

Stated differently, magnetic response distribution visualization device 100 may include one large induction circuit 112 on each side of security gate 111 or a plurality of induction circuits 112 on each side of security gate 111. For example, magnetic response distribution visualization device 100 may include one large coil on each side of security gate 111 as induction circuit 112, or a plurality of coils on each side of security gate 111 as the plurality of induction circuits 112.

Figure 8:
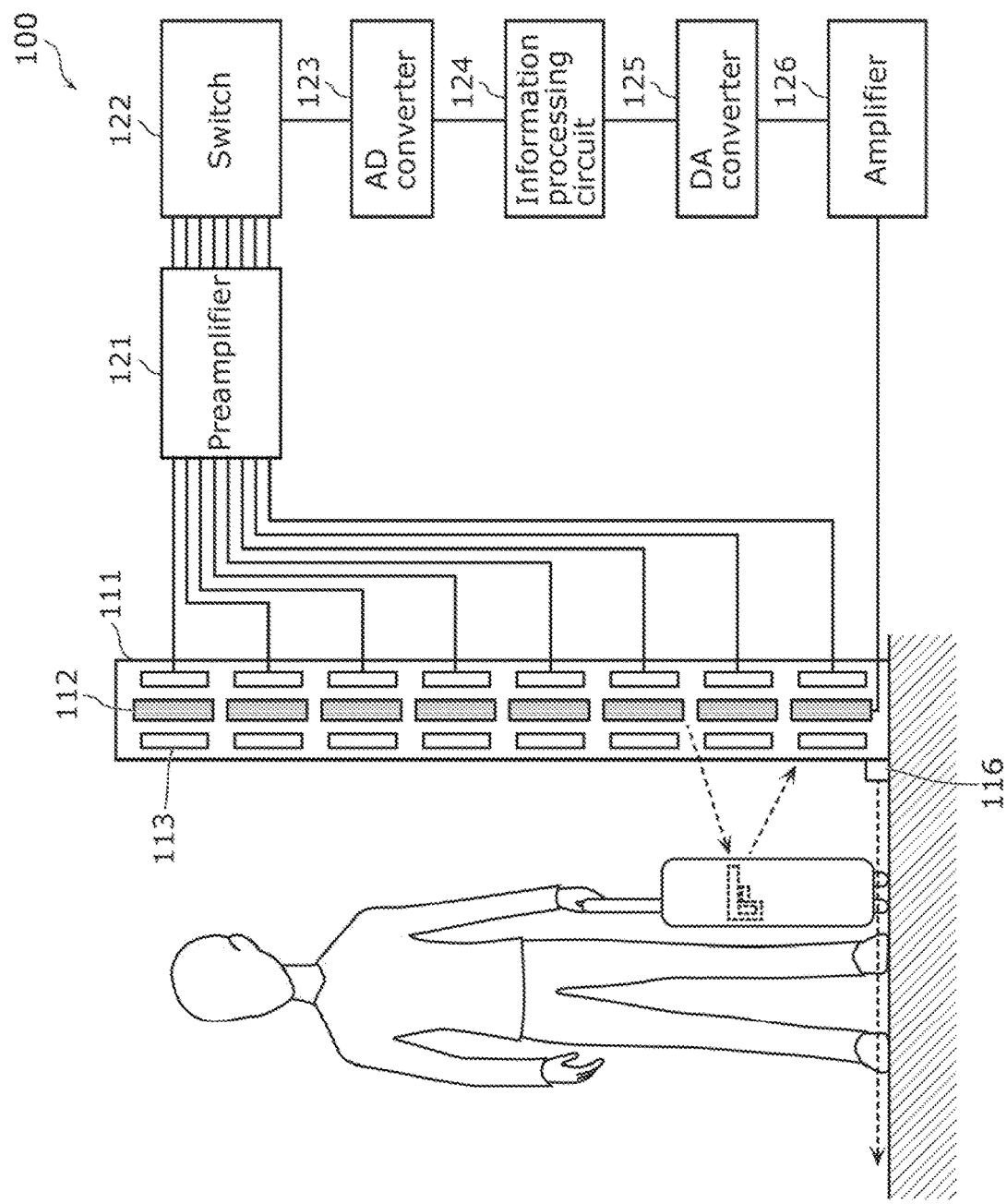
FIG. 8 is a schematic diagram illustrating a first variation of a magnetic response distribution visualization device according to an embodiment of the present disclosure.

FIG. 8 is a schematic diagram illustrating a first variation of magnetic response distribution visualization device 100 illustrated in FIG. 1. In the example in FIG. 8, security gate 111 consists of only one side, i.e., is a single-sided gate. For example, the magnetic field component induced by induction circuit 112 magnetizes the weapon. This causes the weapon to induce a secondary magnetic field component. Magnetic sensor 113, which is disposed on the same side as induction circuit 112, senses the magnetism of the magnetic field including the secondary magnetic field component induced by the weapon.

Stated differently, the magnetic field component induced by induction circuit 112 is altered by the magnetization of the weapon, and the altered magnetic field component is sensed by magnetic sensor 113 on the same side as induction circuit 112. Such an implementation can be referred to as a reflective implementation.

Even in a reflective implementation, magnetic sensor 113 can adequately sense magnetism in the magnetic field including a magnetic field component that changes by the magnetization of the weapon. Accordingly, magnetic response distribution visualization device 100 can appropriately generate an image showing the magnetic response distribution.

Figure 9:
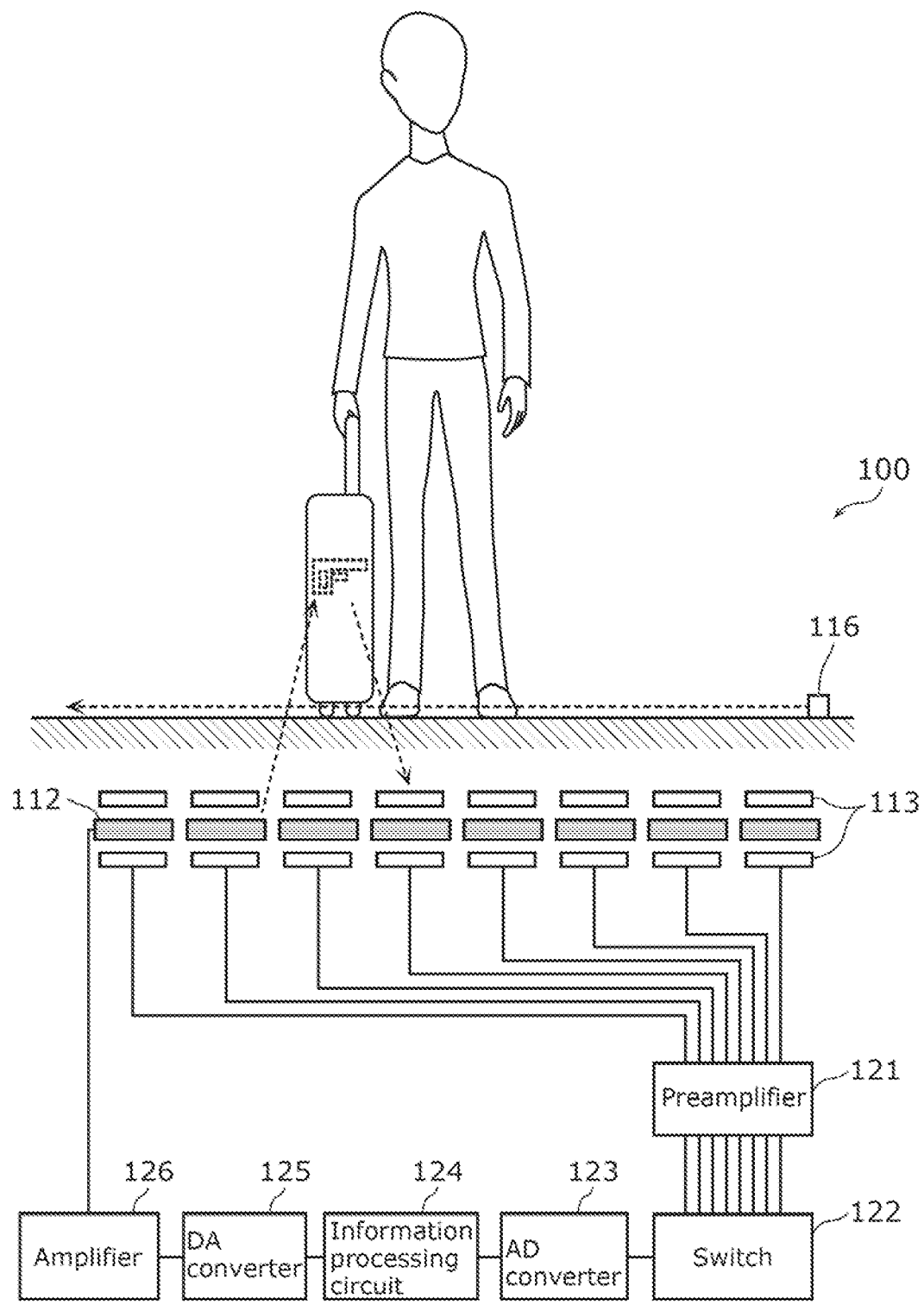
FIG. 9 is a schematic diagram illustrating a second variation of a magnetic response distribution visualization device according to an embodiment of the present disclosure.

FIG. 9 is a schematic diagram illustrating a second variation of magnetic response distribution visualization device 100 illustrated in FIG. 1. In the example in FIG. 9, induction circuit 112 and magnetic sensor 113 are embedded in the floor. With this, magnetic response distribution visualization device 100 can generate an image showing the magnetic response distribution without being noticed by a dangerous person holding a weapon. The implementation in the example in FIG. 9 is also a reflective implementation just like the example in FIG. 8.

Figure 10:
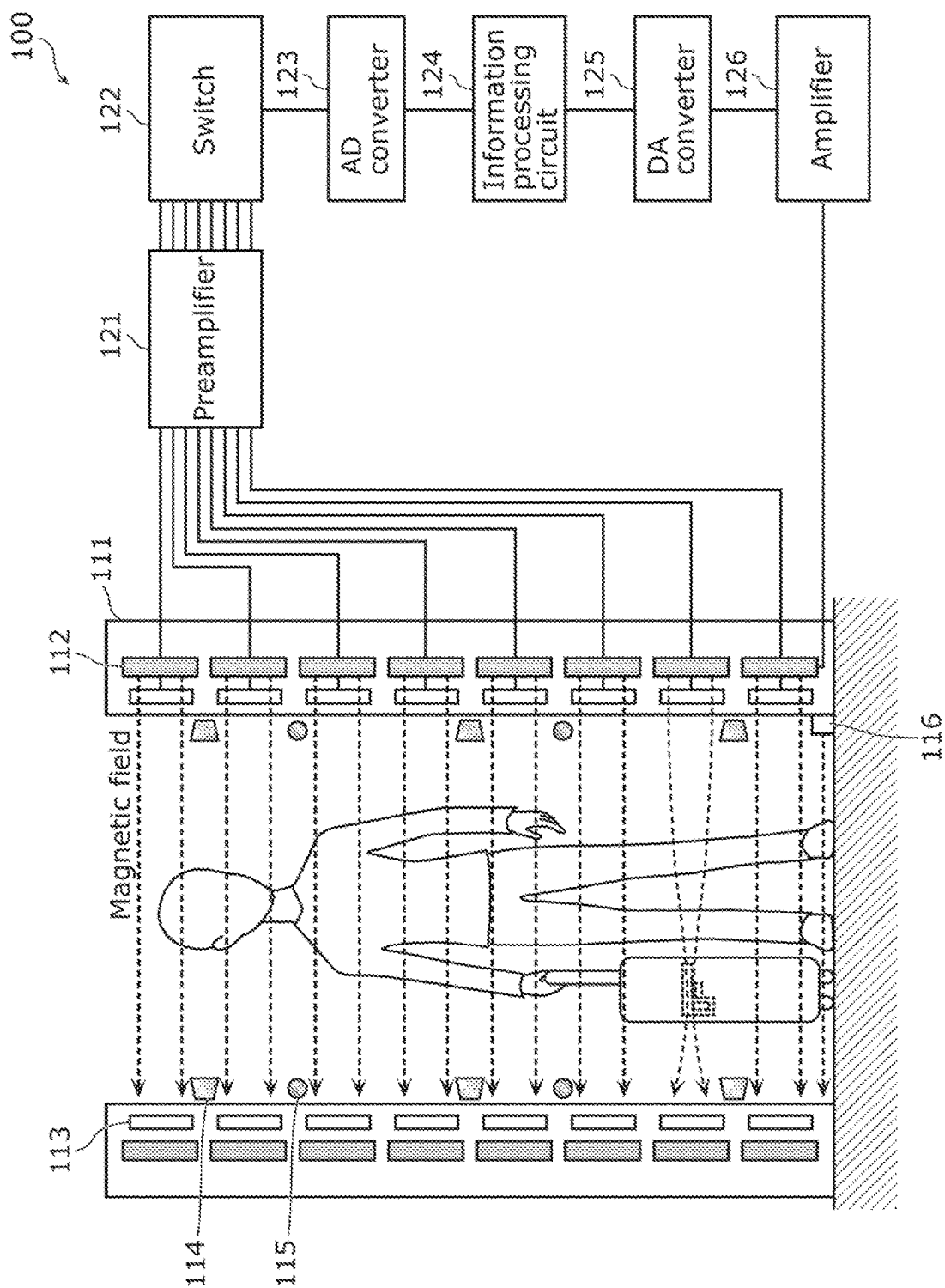
FIG. 10 is a schematic diagram illustrating a third variation of a magnetic response distribution visualization device according to an embodiment of the present disclosure.

FIG. 10 is a schematic diagram illustrating a third variation of magnetic response distribution visualization device 100 illustrated in FIG. 1. Magnetic sensor 113 senses not only magnetism coming from moving objects passing inside security gate 111, but also from matter present outside security gate 111. Such magnetism constitutes noise rather than information about the magnetic response distribution of the moving object.

In the example in FIG. 1, each side of security gate 111 includes two columns of a plurality of magnetic sensors 113. With this, the plurality of magnetic sensors 113 can sense the strength and phase of the magnetic field at two positions at different distances from the moving object passing through security gate 111. Magnetic response distribution visualization device 100 can therefore obtain sensing results in two measurement planes and can obtain a gradient of the sensing results.

Information processing circuit 124 of magnetic response distribution visualization device 100 can then calculate the strength and phase of the magnetic field at a vicinal position near the moving object, via the method described with reference to FIG. 3. With this, information processing circuit 124 can computationally eliminate noise composed of magnetism coming from matter outside security gate 111.

In the example in FIG. 10, each side of security gate 111 includes one column of a plurality of magnetic sensors 113. With this configuration as well, information processing circuit 124 of magnetic response distribution visualization device 100 can calculate the strength and phase of the magnetic field at a vicinal position near the moving object, via a method similar to the method described with reference to FIG. 3.

More specifically, in equation (2) presented as a general solution of the Laplace equation, it is assumed that the magnetism comes from both the forward and reverse z-directions, and includes a term that increases exponentially in the z-direction and a term that attenuates exponentially in the z-direction. If it is assumed that the magnetism comes from one side with respect to the z-direction, the general solution of the Laplace equation can be expressed using one term among a term that increases exponentially in the z-direction and a term that attenuates exponentially in the z-direction. Thus, in this case, the number of unknown terms is reduced to one.

It is therefore possible to solve the Laplace equation using the Dirichlet boundary condition, $H_z(x, y, 0)$, without using the Neumann boundary condition, $\partial/\partial z H_z(x, y, z)|_{z=0}$. Stated differently, even when a plurality of magnetic sensors 113 are configured in a single column on each side, information processing circuit 124 can calculate the strength and phase of the magnetic field at the vicinal position near the moving object.

Note that this does not eliminate noise composed of magnetism coming from matter outside security gate 111. However, in cases in which it can be assumed that there is no influence from noise composed of magnetism coming from matter outside security gate 111, the example in FIG. 10 is also effective.

Figure 11:
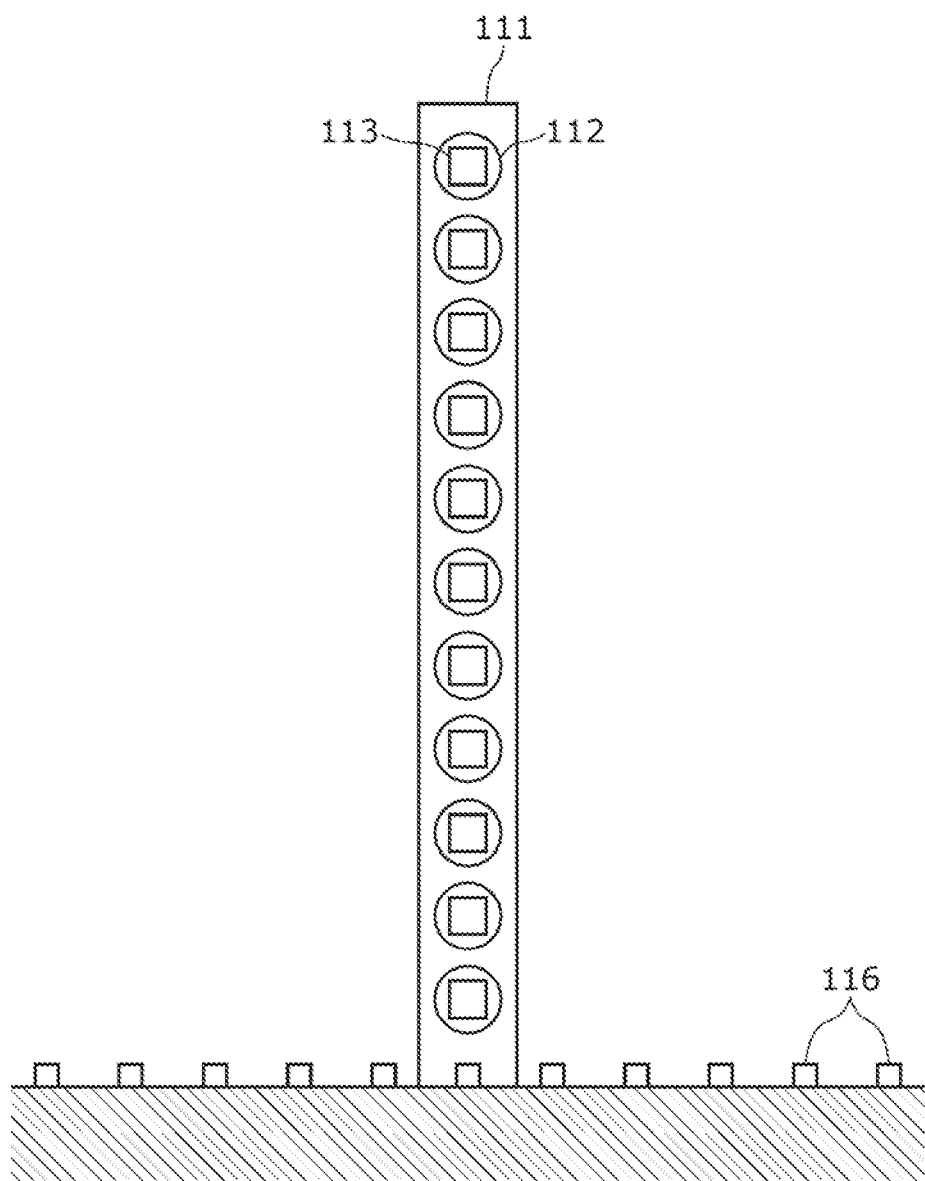
FIG. 11 is a schematic diagram illustrating a first arrangement example of induction circuits and magnetic sensors according to an embodiment of the present disclosure.

FIG. 11 is a schematic diagram illustrating an example of a side surface of security gate 111 illustrated in FIG. 1 and a first arrangement example of induction circuits 112 and magnetic sensors 113. The example in FIG. 11 is the same as the example in FIG. 2. The plurality of induction circuits 112 and the plurality of magnetic sensors 113 are aligned perpendicular to the direction of travel of the moving object.

Stated differently, on one side of security gate 111, groups, each including one induction circuit 112 and one or two magnetic sensors 113, are arranged one-dimensionally. Stated differently, a plurality of these groups form a one-dimensional array.

The plurality of induction circuits 112 arranged one-dimensionally on one side of security gate 111 and the plurality of magnetic sensors 113 arranged one-dimensionally on the other side of security gate 111 scan so as to sandwich the moving object. Alternatively, like in the reflective implementation example, the plurality of induction circuits 112 and the plurality of magnetic sensors 113 may scan the moving object on only one side. The plurality of magnetic sensors 113 sense the magnetism at a plurality of points in time.

For example, the moving speed of the moving object is measured by a plurality of laser devices 116. Temporal changes in the sensing result are then replaced by spatial changes in the sensing result by shifting the position based on the moving speed. With this, a two-dimensional sensing result can be obtained. The two-dimensional sensing result is then used as a boundary condition for the reconstruction process.

Figure 12:
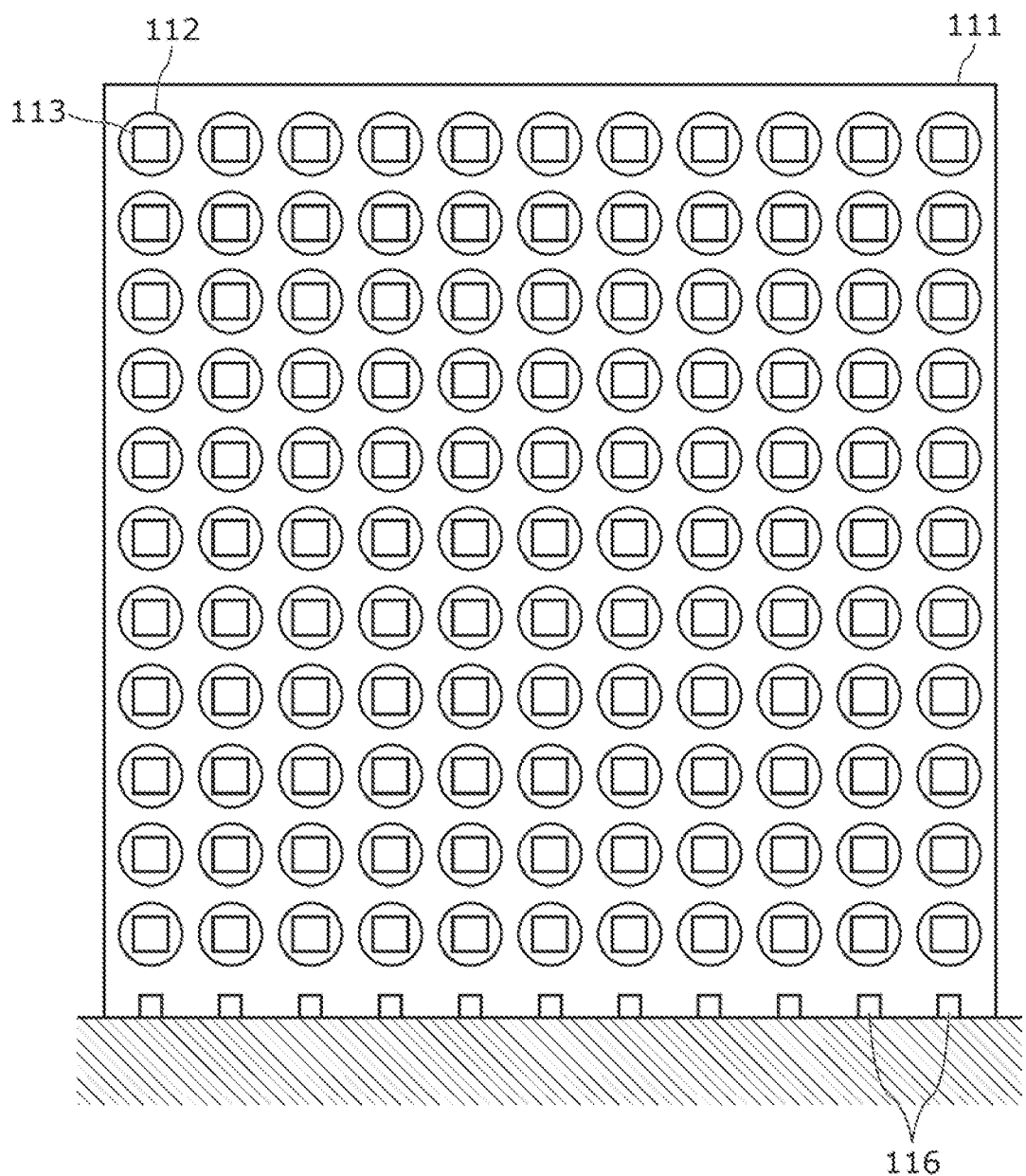
FIG. 12 is a schematic diagram illustrating a second arrangement example of induction circuits and magnetic sensors according to an embodiment of the present disclosure.

FIG. 12 is a schematic diagram illustrating an example of a side surface of security gate 111 illustrated in FIG. 1 and a second arrangement example of induction circuit 112 and magnetic sensor 113.

In the example illustrated in FIG. 12, on one side of security gate 111, groups, each including one induction circuit 112 and one or two magnetic sensors 113, are arranged two-dimensionally. Stated differently, a plurality of these groups form a two-dimensional array.

A plurality of induction circuits 112 arranged two-dimensionally on one side of security gate 111 and a plurality of magnetic sensors 113 arranged two-dimensionally on the other side of security gate 111 scan so as to sandwich the moving object. Alternatively, like in the reflective implementation example, the plurality of induction circuits 112 and the plurality of magnetic sensors 113 may scan the moving object on only one side. The magnetism is sensed at a plurality of points in time, and at each point in time, a two-dimensional sensing result is obtained.

For example, the moving speed of the moving object is measured by a plurality of laser devices 116. The two-dimensional sensing results obtained at the plurality of points in time are then aligned based on the moving speed, and noise and distortion are removed. An integration of the two-dimensional sensing results is then used as a boundary condition for the reconstruction process.

Figure 13:
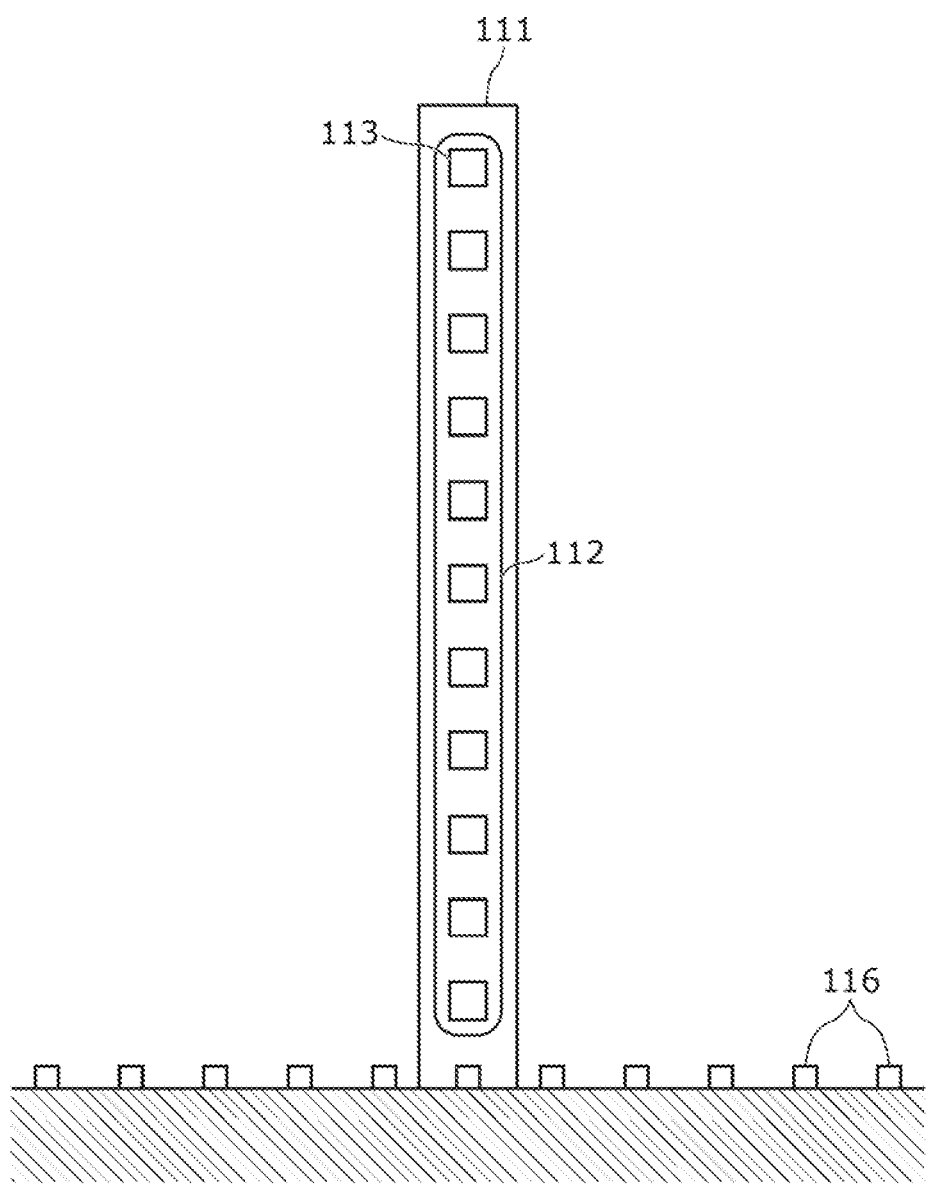
FIG. 13 is a schematic diagram illustrating a third arrangement example of an induction circuit and magnetic sensors according to an embodiment of the present disclosure.

FIG. 13 is a schematic diagram illustrating an example of a side surface of security gate 111 illustrated in FIG. 1 and a third arrangement example of induction circuit 112 and magnetic sensor 113. The example in FIG. 13 is similar to the example in FIG. 11, but specifically corresponds to the example in FIG. 7. Stated differently, one large induction circuit 112 is located on each side. The one large induction circuit 112 is, for example, one large coil.

Stated differently, instead of a plurality of induction circuits 112 that are arranged one-dimensionally in the example illustrated in FIG. 11, one large induction circuit 112, as in the example illustrated in FIG. 13, may be used. One such large induction circuit 112 is capable of performing the same role as the plurality of induction circuits 112 that are arranged one-dimensionally in the example illustrated in FIG. 11.

One large induction circuit 112 may be located on each of the right and left sides of security gate 111, or, like in the reflective implementation example, one large induction circuit 112 may be located on only one side.

Figure 14:
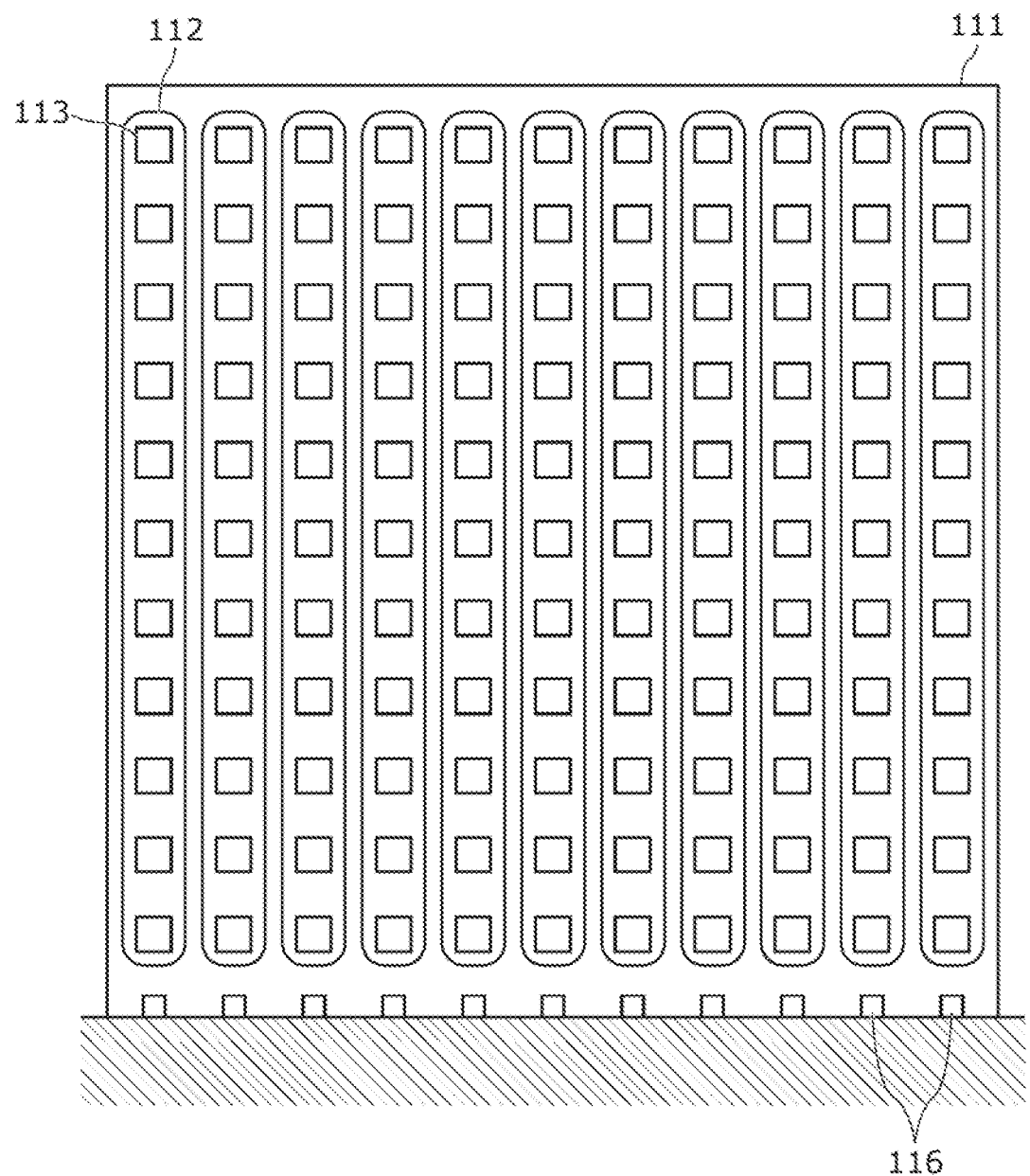
FIG. 14 is a schematic diagram illustrating a fourth arrangement example of induction circuits and magnetic sensors according to an embodiment of the present disclosure.

FIG. 14 is a schematic diagram illustrating an example of a side surface of security gate 111 illustrated in FIG. 1 and a fourth arrangement example of induction circuit 112 and magnetic sensor 113. The example in FIG. 14 is similar to the example in FIG. 12, but in the example in FIG. 14, one induction circuit 112 is provided per vertical line. More specifically, a plurality of vertically elongated induction circuits 112 are aligned horizontally.

Stated differently, instead of a plurality of induction circuits 112 that are arranged two-dimensionally in the example illustrated in FIG. 12, a plurality of vertically elongated induction circuits 112, as in the example illustrated in FIG. 14, may be used. Such vertically elongated induction circuits 112 are capable of performing the same role as the plurality of induction circuits 112 that are arranged two-dimensionally in the example illustrated in FIG. 12.

In the example in FIG. 14, one induction circuit 112 is provided per vertical line, but one induction circuit 112 may be provided per horizontal line. More specifically, a plurality of horizontally elongated induction circuits 112 may be aligned vertically. Such horizontally elongated induction circuits 112 are also capable of performing the same role as the plurality of induction circuits 112 that are arranged two-dimensionally in the example illustrated in FIG. 12.

Figure 15:
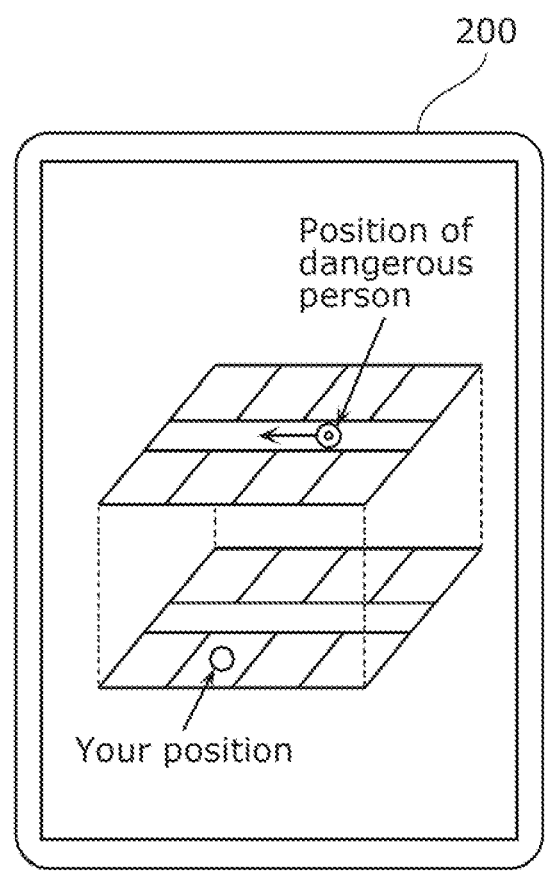
FIG. 15 is a schematic diagram illustrating an example of information displayed on an external terminal according to an embodiment of the present disclosure.

FIG. 15 is a schematic diagram illustrating an example of information displayed on external terminal 200 illustrated in FIG. 5. In the example illustrated in FIG. 15, external terminal 200 is a smartphone possessed by the police or a citizen.

For example, information processing circuit 124 of magnetic response distribution visualization device 100 generates an image showing the magnetic response distribution based on sensing results obtained from the plurality of magnetic sensors 113 in each of the plurality of security gates 111. If a weapon is recognized from the image, information processing circuit 124 identifies and locates security gate 111 that is the source of the image from which the weapon was recognized, from among the plurality of security gates 111.

Information processing circuit 124 may transmit the location of the identified security gate 111 to external terminal 200 as the location of the dangerous person in possession of the weapon. External terminal 200 may receive information indicating the location of the dangerous person and display the location of the dangerous person.

Alternatively, information processing circuit 124 may further identify the location of the dangerous person based on the location of the identified security gate 111 and the moving speed obtained by laser device 116, etc., in the vicinity. More specifically, information processing circuit 124 may identify the location of the dangerous person by shifting, from the location of security gate 111, a distance calculated by multiplying the difference between the sensing time and the current time and the moving speed. Information processing circuit 124 may then transmit the identified location to external terminal 200.

Here, the direction of movement may be identified based on a rule, such as one-way traffic, or may be obtained by, for example, camera 114, infrared sensor 115, or laser device 116.

Information processing circuit 124 may also transmit information indicating the moving speed obtained by, for example, laser device 116 to external terminal 200. External terminal 200 may receive information and display the moving speed indicated by the received information as the moving speed of the dangerous person.

External terminal 200 may display the various types of information described above as augmented reality (AR) images.

Figure 16:
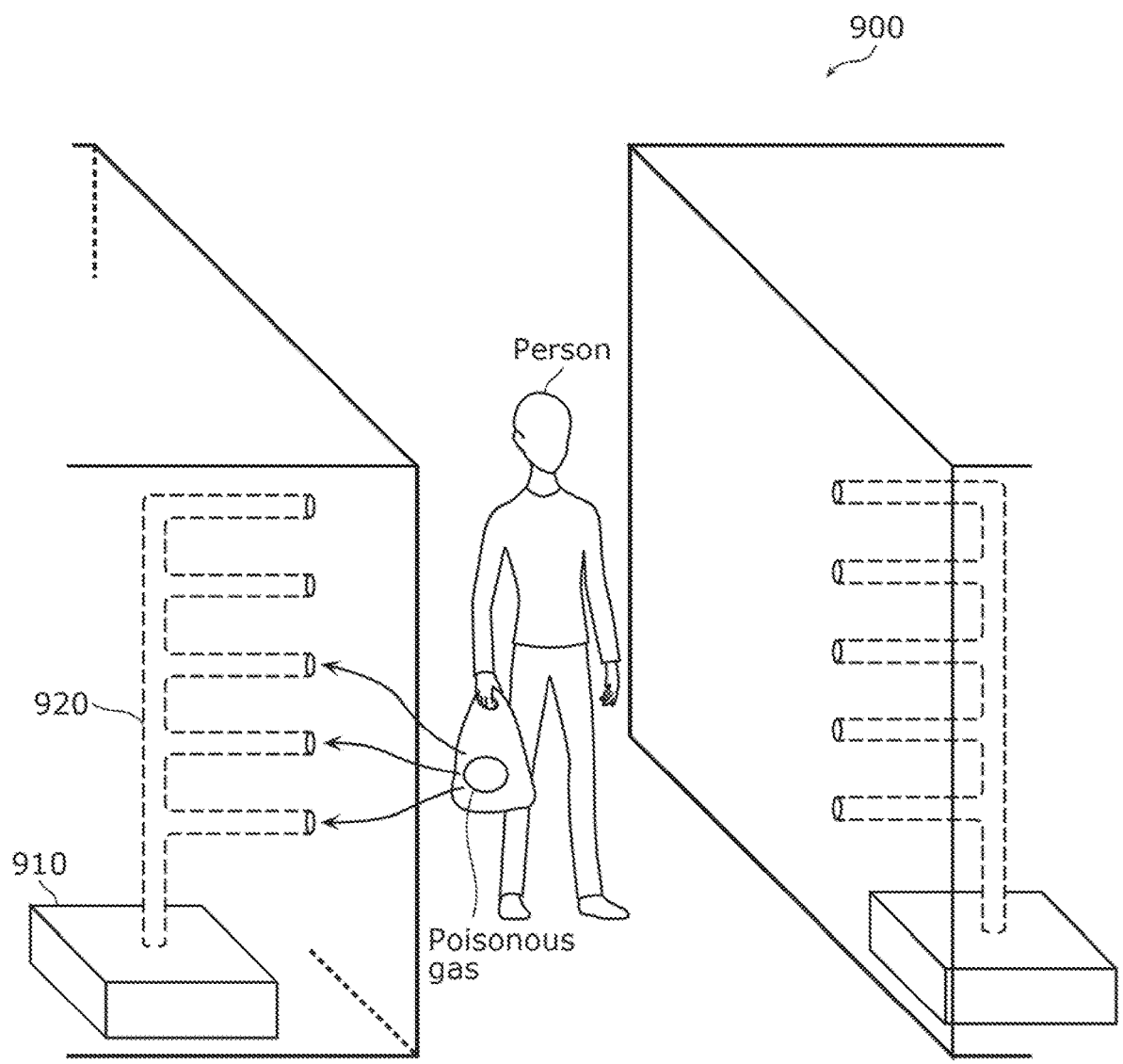
FIG. 16 is a schematic diagram illustrating an example of a security inspection system according to an embodiment of the present disclosure.

FIG. 16 is a schematic diagram illustrating an example of a security inspection system that uses magnetic response distribution visualization device 100 illustrated in FIG. 1.

For example, security inspection system 900 illustrated in FIG. 16 includes magnetic response distribution visualization device 100. Security inspection system 900 measures the quasi-static magnetic field, solves the inverse problem analytically, and reconstructs an image of the field. This enables security inspection system 900 to non-invasively visualize weapons such as blades or firearms concealed in bags, clothes, between clothes and a living body, or inside living bodies, etc., in real time.

Security inspection system 900 further includes gas-phase chemical agent analyzer 910 and pipe 920 to analyze gasoline or poison gas in real time. For example, microscopic holes are one- or two-dimensionally formed in a wall surface and the surrounding air is sucked into multiple channels. The air sucked in is sent to gas-phase chemical agent analyzer 910 through pipe 920.

For example, gas-phase chemical agent analyzer 910 may include a gas chromatographer, a mass spectrometer, an ion mobility analyzer, or a combination of two or more of these, and may also be referred to as a gas classification detector. Gas-phase chemical agent analyzer 910 identifies the air sent to gas-phase chemical agent analyzer 910 and analyzes risk.

Gas-phase chemical agent analyzer 910 shares information on the communication network about the person in possession of the poison gas just like the information about the person in possession of a weapon such as a blade or firearm as described above. Gas-phase chemical agent analyzer 910 may report information about such a dangerous person to the police or other crisis management personnel, and may include such information about the dangerous person in instructions for evacuation routes for citizens in the vicinity.

Note that FIG. 16 is merely a schematic diagram, and the number and size of the holes leading to gas-phase chemical agent analyzer 910 via pipe 920 may be different from the example in FIG. 16. A larger number of smaller holes may be formed in a denser manner.

Gas-phase chemical agent analyzer 910 and pipe 920 may also be included in security gate 111 illustrated in FIG. 1. Gas-phase chemical agent analyzer 910 and pipe 920 may be included in each side of security gate 111, in one side only, in the floor, or in a pole.

Security inspection system 900 may include a thermographic device. Security inspection system 900 may include equipment to perform real-time diagnostic imaging on a person who may be a carrier of a virus, such as a coronavirus, based on sensing results obtained from the thermographic device. More specifically, diagnostic imaging is performed on a person passing through security gate 111.

Magnetic response distribution visualization device 100 may operate as equipment for performing such diagnostic imaging. Moreover, the thermographic device may operate as equipment for performing such diagnostic imaging. Magnetic response distribution visualization device 100 may include a thermographic device. Moreover, a thermographic device may be included in camera 114 and the like.

For example, information processing circuit 124 may generate and output images for diagnostic imaging by reflecting the moving speed of the moving object in the sensing results obtained from the thermographic device at each time point, just as with the sensing results obtained from magnetic sensor 113 at each time point.

Figure 17:
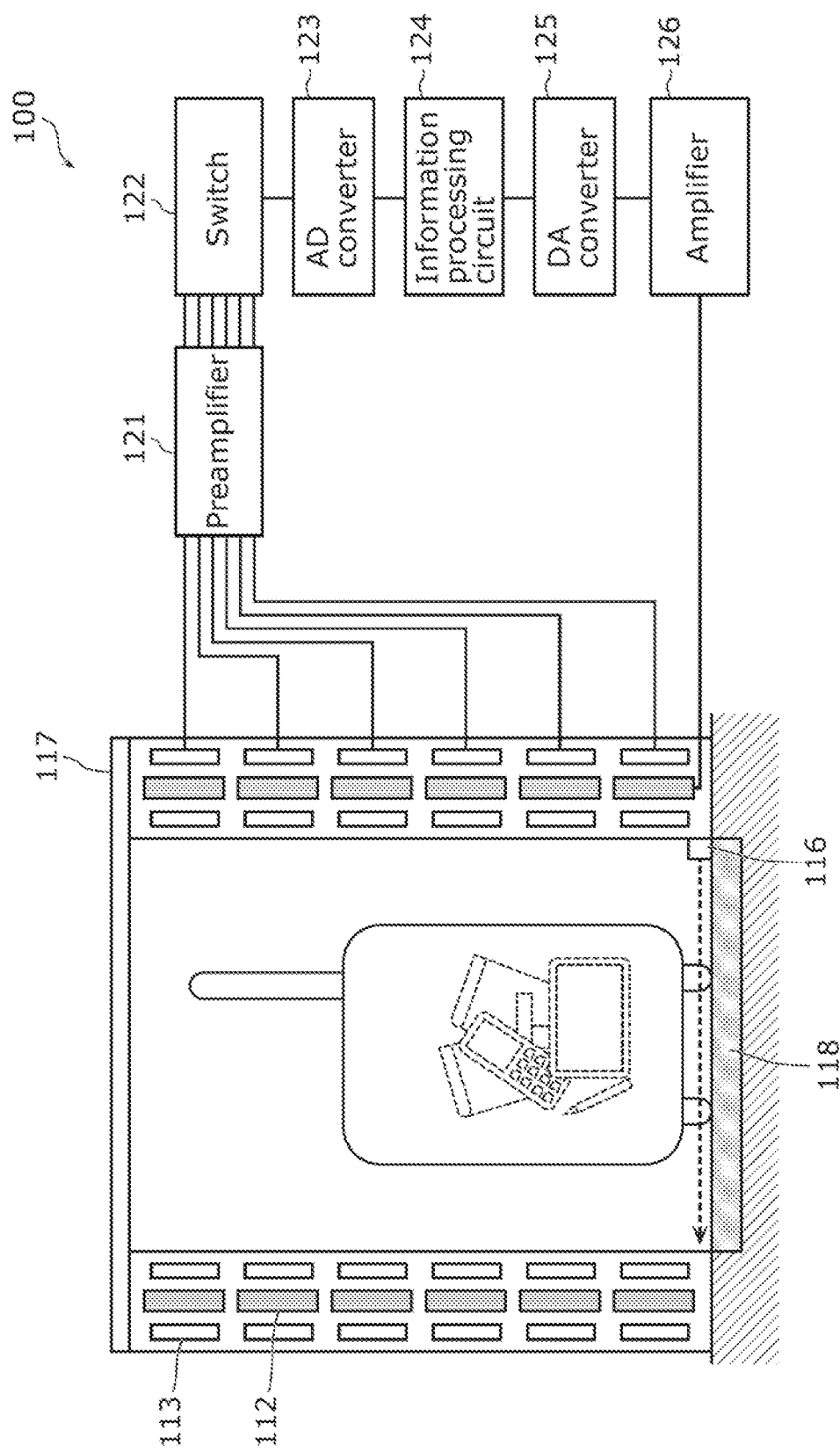
FIG. 17 is a schematic diagram illustrating a fourth variation of a magnetic response distribution visualization device according to an embodiment of the present disclosure.

FIG. 17 is a schematic diagram illustrating a fourth variation of magnetic response distribution visualization device 100 illustrated in FIG. 1. In the example in FIG. 17, magnetic response distribution visualization device 100 is used for luggage inspection at, for example, an airport. In the example in FIG. 1, the moving object is a person and luggage, etc., carried by the person, but in the example in FIG. 17, the moving object is luggage.

For example, the luggage passes through the interior of frame 117 on conveyor belt 118. Magnetic response distribution visualization device 100 generates an image showing the magnetic response distribution of the luggage. The principle for generating an image showing the magnetic response distribution is the same as in the example in FIG. 1.

The moving speed obtained by laser device 116 may be used in this example as well. Instead of laser device 116, the moving speed may be obtained by camera 114 or infrared sensor 115, etc., as illustrated in FIG. 1. Alternatively, a moving speed determined by the specifications of conveyor belt 118 may be used. If a moving speed determined by the specifications of conveyor belt 118 is used, magnetic response distribution visualization device 100 does not need to include, for example, laser device 116.

Laser device 116, etc., is particularly effective in cases where conveyor belt 118 is not used and a person passes the luggage through, or where the operating speed of conveyor belt 118 is indefinite.

The plurality of induction circuits 112 and the plurality of magnetic sensors 113 may be arranged one-dimensionally, as in FIG. 11, or two-dimensionally, as in FIG. 12. When the plurality of induction circuits 112 and the plurality of magnetic sensors 113 are arranged one-dimensionally, a two-dimensional sensing result is obtained as the plurality of induction circuits 112 and the plurality of magnetic sensors 113 scan the moving luggage relative to each other. Then, using the two-dimensional sensing result as a boundary condition, the strength and phase of the magnetic field at a vicinal position of the luggage are calculated, and an image showing the magnetic response distribution of the luggage is generated.

The plurality of induction circuits 112 and the plurality of magnetic sensors 113 may be provided on one side only, as in FIG. 8. This configuration can also generate images showing the magnetic response distribution of the luggage. The plurality of magnetic sensors 113 may be arranged in one column on each side, as in FIG. 10.

Figure 18:
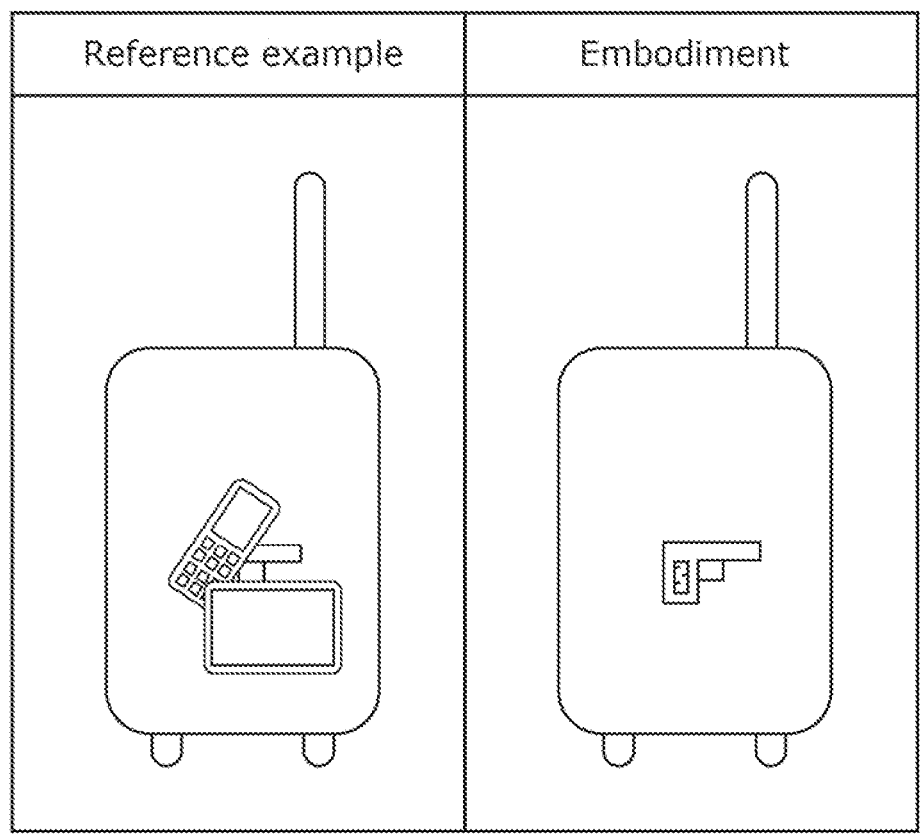
FIG. 18 is a schematic diagram illustrating an image obtained according to a reference example and an image obtained according to an embodiment of the present disclosure.

FIG. 18 is a schematic diagram illustrating an image obtained according to a reference example and an image obtained according to the present embodiment.

For example, X-rays are sometimes used for luggage inspection at, for example, airports. The image obtained by X-rays shows all metals. More specifically, the image shows electronic products such as cell phones, portable terminals, smartphones, or tablets, which are typically carried by a person (see "reference example" in FIG. 18). It is therefore not easy to detect a weapon. Artificial intelligence (AI) is also not effective with low-contrast images.

The image according to the present embodiment does not show electronic products, but shows weapons (see "embodiment" in FIG. 18). It is therefore effective in preventing mistakes at, for example, airports.

As described above, magnetic response distribution visualization device 100 according to each example of the present embodiment can appropriately calculate the strength and phase of the magnetic field in the vicinity of a moving object based on the moving speed of the moving object, the sensing result of the magnetism, and the fundamental equation for a field. Magnetic response distribution visualization device 100 can then generate an image showing the magnetic response distribution with high accuracy as an image to be used for security inspections, based on the calculation result of the strength and phase of the magnetic field.

One of the left and right sides of security gate 111 may include a plurality of induction circuits 112 and the other side may include a plurality of magnetic sensors 113. The magnetic field component may always be induced on one side and magnetism may be sensed on the other side, without having to switch between left and right side operations. This may be applied to the luggage inspection example illustrated in FIG. 17. The reflective implementation operations may be switched between the left and right sides.

Security gate 111 described above may be included in a wall. Stated differently, both sides of a passage may contain a plurality of induction circuits 112 and a plurality of magnetic sensors 113, or only one side of a passage may contain a plurality of induction circuits 112 and a plurality of magnetic sensors 113.

Although a magnetic field is exemplified in the above description, the concepts of the present disclosure are applicable to any field that satisfies the Laplace equation, which is the fundamental equation for a field. In particular, the concepts of the present disclosure are applicable to static or quasi-static fields. A quasi-static field may be a substantially static field, such as an electromagnetic field of 100 kHz or less, which can be regarded as having no wave properties. More specifically, an electric field may be used instead of a magnetic field. The scope of application of the concepts of the present disclosure may be extended to temperature and pressure fields, etc.

Therefore, the above magnetic response distribution visualization device (100) may be described as an external field response distribution visualization device (100). For example, the external field response distribution visualization device (100) generates an image showing the external field response distribution, which is a distribution of responses to an external field. The magnetic sensor (113) described above may be a sensor (113) that senses the strength and phase of a field. Instead of magnetic strength, the strength and phase of a field can be used.

In other words, "magnetic field" in the above description can be replaced with simply "field", and "magnetic response distribution" can be replaced with "external field response distribution".

Figure 19:
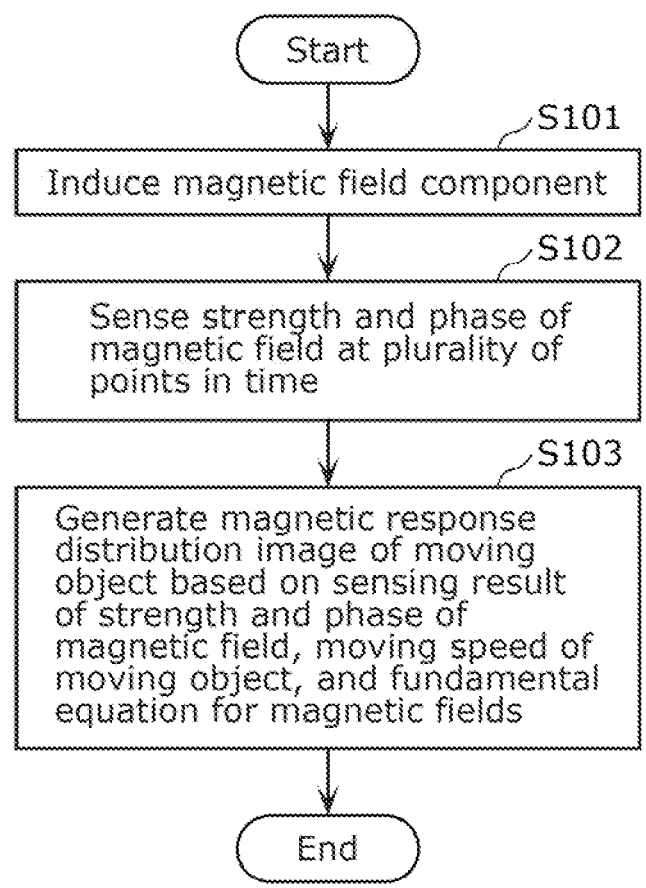
FIG. 19 is a flowchart showing an operation of a magnetic response distribution visualization device according to an embodiment of the present disclosure.

FIG. 19 is a flowchart showing an operation of a magnetic response distribution visualization device (100) according to the present embodiment.

For example, an induction circuit (112) induces, from outside a moving object, a magnetic field component that is a component of a magnetic field that satisfies the fundamental equation for magnetic fields (S101). The sensor (113) senses a strength and a phase of the magnetic field including the magnetic field component altered by the moving object, at a plurality of points in time outside the moving object (S102).

The information processing circuit (124) detects a strength and a phase of the magnetic field at a vicinal position closer to the moving object than the sensor (113), based on the sensing result of the strength and the phase of the magnetic field, the moving speed of the moving object, and the fundamental equation for magnetic fields. The information processing circuit (124) generates, based on the calculation result of the strength and the phase of the magnetic field, a magnetic response distribution image that shows a distribution of a response of the moving object to the magnetic field component induced by the induction circuit (112) and is used for security inspection (S103).

With this, the magnetic response distribution visualization device (100) can appropriately calculate the strength and the phase of the magnetic field in the vicinity of the moving object based on: positions of the sensor (113) defined relatively at a plurality of points in time based on the moving speed; the sensing result of the strength and the phase of the magnetic field; and the fundamental equation for magnetic fields. The magnetic response distribution visualization device (100) can generate a magnetic response distribution image with high accuracy based on the calculation result of the strength and phase of the magnetic field.

Stated differently, the magnetic response distribution visualization device (100) can generate an image showing the distribution of the response of the moving object to an external field with high accuracy as an image to be used for security inspection.

For example, the information processing circuit (124) may identify, at each of the plurality of points in time, a sensing position defined as a position of the sensor (113) relative to the moving object, based on the moving speed, to identify a plurality of sensing positions of the sensor (113) relative to the moving object at the plurality of points in time. The information processing circuit (124) may calculate the strength and the phase of the magnetic field at the vicinal position by using temporal changes in the sensing result over the plurality of points in time as spatial changes in the sensing result across the plurality of sensing positions.

This enables the magnetic response distribution visualization device (100) to use temporal changes in sensing results as spatial changes. The magnetic response distribution visualization device (100) can therefore appropriately calculate a spatial distribution and can appropriately calculate the strength and the phase of the magnetic field at a vicinal position near the moving object.

For example, the information processing circuit (124) may determine whether the moving object includes a detection target object based on the magnetic response distribution image. When information processing circuit (124) determines that the moving object includes the detection target object, the information processing circuit (124) may output information indicating the location of the detection target object or the location of the moving object to an external terminal (200). This enables the magnetic response distribution visualization device (100) to notify of the location of a specific detection target object or the location of the moving object including a specific detection target object.

For example, the magnetic response distribution visualization device (100) may further include an instrument (114, 115, 116) that measures the moving speed. This enables the magnetic response distribution visualization device (100) to appropriately obtain the moving speed of the moving object.

For example, the magnetic field component induced by the induction circuit (112) may be a periodically varying magnetic field component. The information processing circuit (124) may detect, from the sensing result, a magnetic field component having the same frequency as the frequency of the periodically varying magnetic field component. The information processing circuit (124) may calculate the strength and the phase of the magnetic field at the vicinal position based on the detected magnetic field component, the moving speed, and the fundamental equation for magnetic fields.

This enables the magnetic response distribution visualization device (100) to appropriately obtain the response to the magnetic field component induced by the induction circuit (112). Stated differently, the magnetic response distribution visualization device (100) can inhibit noise. The magnetic response distribution visualization device (100) can therefore generate a magnetic response distribution image with high accuracy.

For example, the magnetic field component induced by the induction circuit (112) may comprise a first magnetic field component and a second magnetic field component. The first magnetic field component has a first frequency and penetrates shielding in the moving object. The second magnetic field component has a second frequency higher than the first frequency and is shielded by the shielding in the moving object.

The information processing circuit (124) may generate a first image showing a distribution of a response of the moving object to the first magnetic field component induced by the induction circuit (112) and a second image showing a distribution of a response of the moving object to the second magnetic field component induced by the induction circuit (112). The information processing circuit (124) may generate the magnetic response distribution image by combining the first image and the second image.

This enables the magnetic response distribution visualization device (100) to generate, as a magnetic response distribution image, a composite image of two images obtained for magnetic field components having two different frequencies. This composite image can both show what is behind the shielding and show the shielding itself. Stated differently, this composite image can properly show the location of an object hidden by the shielding. The magnetic response distribution visualization device (100) can therefore generate a magnetic response distribution image that is effective for security inspection.

For example, the sensor (113) may comprise a plurality of sensors (113) disposed on a straight line. This enables the magnetic response distribution visualization device (100) to sense the strength and the phase of the magnetic field using a one-dimensional sensor array. This makes it possible to reduce the space required for providing the sensors (113).

For example, the sensor (113) may comprise a plurality of sensors (113) disposed on a first straight line and a plurality of sensors (113) disposed on a second straight line that is parallel to the first straight line and farther from the moving object than the first line is. This enables the magnetic response distribution visualization device (100) to sense the strength and the phase of the magnetic field using two one-dimensional sensor arrays, and sense the strength and the phase of the magnetic field at sensing positions at different distances from the moving object.

For example, the induction circuit (112) may comprise a plurality of induction circuits (112) disposed on a straight line. This enables the magnetic response distribution visualization device (100) to induce a magnetic field component using a one-dimensional induction circuit array. This makes it possible to reduce the space required for providing the induction circuits (112).

For example, the sensor (113) may comprise a plurality of sensors (113) disposed on a plane. This enables the magnetic response distribution visualization device (100) to sense the strength and the phase of the magnetic field using a two-dimensional sensor array. This enables the magnetic response distribution visualization device (100) to obtain a two-dimensional sensing result at a single point in time. The magnetic response distribution visualization device (100) can therefore combine two-dimensional sensing results obtained at a plurality of points in time to eliminate noise.

For example, the sensor (113) may comprise a plurality of sensors (113) disposed on a first plane and a plurality of sensors (113) disposed on a second plane that is parallel to the first plane and farther from the moving object than the first plane is. This enables the magnetic response distribution visualization device (100) to sense the strength and the phase of the magnetic field using two two-dimensional sensor arrays, and sense the strength and the phase of the magnetic field at sensing positions at different distances from the moving object.

For example, the induction circuit (112) may comprise a plurality of induction circuits (112) disposed on a plane. This enables the magnetic response distribution visualization device (100) to uniformly induce a magnetic field component using a two-dimensional induction circuit array.

For example, the induction circuit (112) and the sensor (113) may be disposed on opposite sides of a path of travel of the moving object. This enables the magnetic response distribution visualization device (100) to sense the strength and the phase of the magnetic field at the sensor (113) which is located on the opposite side of the moving object relative to the induction circuit (112). With this, when sensing the strength and phase of the magnetic field using the sensor (113), the magnetic response distribution visualization device (100) can inhibit the influence of direct magnetic field components induced by the induction circuit (112) that have not been affected by the moving object.

For example, the induction circuit (112) and the sensor (113) may be disposed on the same side of a path of travel of the moving object and not on opposite sides of the path of travel. This enables the magnetic response distribution visualization device (100) to sense the strength and the phase of the magnetic field at the sensor (113) which is located on the same side of the moving object relative to the induction circuit (112). The space required for providing the induction circuit (112) and the sensor (113) can therefore be reduced.

For example, the induction circuit (112) may comprise a plurality of induction circuits (112) disposed on first and second opposite sides of a path of travel of the moving object. The sensor (113) may comprise a plurality of sensors (113) disposed on the first side and the second side.

The information processing circuit (124) may switch between a first operation and a second operation. Here, the first operation is an operation in which one or more of the plurality of induction circuits (112) disposed on the first side induce the magnetic field component and one or more of the plurality of sensors (113) disposed on the second side sense the strength and the phase of the magnetic field. The second operation is an operation in which one or more of the plurality of induction circuits (112) disposed on the second side induce the magnetic field component and one or more of the plurality of sensors (113) disposed on the first side sense the strength and the phase of the magnetic field.

This enables the magnetic response distribution visualization device (100) to sense the strength and the phase of the magnetic field using time division on both sides, making it possible to obtain a lot of information.

For example, the information processing circuit (124) may select, as the magnetic response distribution image, either a first magnetic response distribution image generated based on the first operation or a second magnetic response distribution image generated based on the second operation. This enables the magnetic response distribution visualization device (100) to adaptively use one of the two magnetic response distribution images corresponding to both sides.

For example, a security inspection system (900) may include: the magnetic response distribution visualization device (100); and a thermographic device for performing diagnostic imaging on a person corresponding to the moving object. This enables the security inspection system (100) to generate an image showing the distribution of the response of a moving object to an external field with high accuracy as an image to be used for security inspection, and to perform diagnostic imaging on a person who may be carrying a virus.

For example, the phase of the magnetic field is the phase related to a periodical change in the magnetic field. In the above description, the phase of the magnetic field is taken into account, but the phase of the magnetic field need not be considered. In other words, the phase of the magnetic field may be omitted. The luminance of the reconstructed image may correspond to the strength of the magnetic field. The strength and the phase of the magnetic field may be replaced by the value of the magnetic field or information on the magnetic field, etc.

Hereinbefore, an aspect of the magnetic response distribution visualization device has been described based on embodiments, but aspects of the magnetic response distribution visualization device are not limited to the embodiments. Various modifications conceivable by those skilled in the art may be made to the embodiments, and elements in the embodiments may be combined discretionarily.

For example, a process executed by a specific element in an embodiment may be executed by a different element instead. Moreover, the processing order of the processes may be changed, and the processes may be performed in parallel. A plurality of variations may also be applied in combination. The ordinal numbers used in the description, such as first, second, etc., may be replaced as appropriate. The ordinal number may be given anew to or removed from element names, etc.

A magnetic response distribution visualization method including steps performed by the elements included in the magnetic response distribution visualization device may be executed by an arbitrary device or system. For example, part or all of the magnetic response distribution visualization method may be executed by a computer including, for example, a processor, memory, and an input/output circuit. In such cases, the magnetic response distribution visualization method may be executed by a program for causing a computer to execute the magnetic response distribution visualization method being executed by the computer.

The program may be recorded on a non-transitory computer-readable recording medium.

Each of the elements of the magnetic response distribution visualization device may be configured in the form of dedicated hardware, in the form of general-purpose hardware that executes the above program or the like, or any combination thereof. For example, the general-purpose hardware may be configured in the form of memory on which a program is recorded and a general-purpose processor that reads the program from the memory and executes the program. Here, the memory may be semiconductor memory or a hard disk, and the general-purpose processor may be a central processing unit (CPU) or the like.

The dedicated hardware may be configured in the form of memory and a dedicated processor or the like. For example, the dedicated processor may reference the memory for recording the measurement data and execute the magnetic response distribution visualization method described above.

Each of the elements of the magnetic response distribution visualization device may be an electrical circuit. The electrical circuits may collectively form a single electrical circuit and, alternatively, may form individual electrical circuits. These electrical circuits may correspond to dedicated hardware or general-purpose hardware that executes the above program, for example.

The magnetic response distribution visualization device can also be described as an image generation device. The magnetic response distribution visualization device may be a security inspection device, such as a body scanner or a luggage inspection device, or may be included in a security inspection device. The magnetic response distribution visualization device may consist of a plurality of dispersed devices. The magnetic response distribution visualization device can also be described as a magnetic response distribution visualization system.

INDUSTRIAL APPLICABILITY

One aspect of the present disclosure is useful for magnetic response distribution visualization devices that generate images showing magnetic response distribution, and is applicable to body scanners, luggage inspection devices, and security inspection devices.

REFERENCE SIGNS LIST 100 magnetic response distribution visualization device (external field response distribution visualization device)
111 security gate
112 induction circuit
113 magnetic sensor (sensor)
114 camera
115 infrared sensor
116 laser device
117 frame
118 conveyor belt
121 preamplifier
122 switch
123 AD converter
124 information processing circuit
125 DA converter
126 amplifier
200 external terminal
900 security inspection system
910 gas-phase chemical agent analyzer
920 pipe

The invention claimed is:

1. A magnetic response distribution visualization device comprising:
    an induction circuit that induces, from outside a moving object, a magnetic field component that is a component of a magnetic field that satisfies a fundamental equation for magnetic fields;
    a sensor that senses a strength and a phase of the magnetic field including the magnetic field component altered by the moving object, at a plurality of points in time outside the moving object; and
    an information processing circuit that, based on a sensing result of the strength and the phase of the magnetic field, a moving speed of the moving object, and the fundamental equation for magnetic fields, calculates a strength and a phase of the magnetic field at a vicinal position closer to the moving object than the sensor, and generates, based on a calculation result of the strength and the phase of the magnetic field, a magnetic response distribution image that shows a distribution of a response of the moving object to the magnetic field component induced by the induction circuit and is used for security inspection.

2. The magnetic response distribution visualization device according to claim 1, wherein
    the information processing circuit:
        identifies, at each of the plurality of points in time, a sensing position defined as a position of the sensor relative to the moving object, based on the moving speed, to identify a plurality of sensing positions of the sensor relative to the moving object at the plurality of points in time; and
        calculates the strength and the phase of the magnetic field at the vicinal position by using temporal changes in the sensing result over the plurality of points in time as spatial changes in the sensing result across the plurality of sensing positions.

3. The magnetic response distribution visualization device according to claim 1, wherein
    the information processing circuit determines whether the moving object includes a detection target object based on the magnetic response distribution image, and when the moving object is determined to include the detection target object, outputs information indicating a location of the detection target object or a location of the moving object to an external terminal.

4. The magnetic response distribution visualization device according to claim 1, further comprising:
    an instrument that measures the moving speed.

5. The magnetic response distribution visualization device according to claim 1, wherein
    the magnetic field component induced by the induction circuit is a periodically varying magnetic field component, and
    the information processing circuit detects, from the sensing result, a magnetic field component having a same frequency as a frequency of the periodically varying magnetic field component, and calculates the strength and the phase of the magnetic field at the vicinal position based on the detected magnetic field component, the moving speed, and the fundamental equation for magnetic fields.

6. The magnetic response distribution visualization device according to claim 5, wherein
    the magnetic field component induced by the induction circuit comprises a first magnetic field component that has a first frequency and penetrates a shielding in the moving object and a second magnetic field component that has a second frequency higher than the first frequency and is shielded by the shielding in the moving object, and
    the information processing circuit generates the magnetic response distribution image by generating a first image showing a distribution of a response of the moving object to the first magnetic field component induced by the induction circuit and a second image showing a distribution of a response of the moving object to the second magnetic field component induced by the induction circuit, and combining the first image and the second image.

7. The magnetic response distribution visualization device according to claim 1, wherein
    the sensor comprises a plurality of sensors disposed on a straight line.

8. The magnetic response distribution visualization device according to claim 1, wherein the sensor comprises a plurality of sensors disposed on a first straight line and a plurality of sensors disposed on a second straight line that is parallel to the first straight line and farther from the moving object than the first line is.

9. The magnetic response distribution visualization device according to claim 7, wherein
the induction circuit comprises a plurality of induction circuits disposed on a straight line.

10. The magnetic response distribution visualization device according to claim 1, wherein
the sensor comprises a plurality of sensors disposed on a plane.

11. The magnetic response distribution visualization device according to claim 1, wherein
the sensor comprises a plurality of sensors disposed on a first plane and a plurality of sensors disposed on a second plane that is parallel to the first plane and farther from the moving object than the first plane is.

12. The magnetic response distribution visualization device according to claim 10, wherein
the induction circuit comprises a plurality of induction circuits disposed on a plane.

13. The magnetic response distribution visualization device according to claim 1, wherein
the induction circuit and the sensor are disposed on opposite sides of a path of travel of the moving object.

14. The magnetic response distribution visualization device according to claim 1, wherein
the induction circuit and the sensor are disposed on a same side of a path of travel of the moving object and not on opposite sides of the path of travel.

15. The magnetic response distribution visualization device according to claim 1, wherein
the induction circuit comprises a plurality of induction circuits disposed on first and second opposite sides of a path of travel of the moving object,
the sensor comprises a plurality of sensors disposed on the first side and the second side, and
the information processing circuit switches between a first operation in which one or more of the plurality of induction circuits disposed on the first side induce the magnetic field component and one or more of the plurality of sensors disposed on the second side sense the strength and the phase of the magnetic field, and a second operation in which one or more of the plurality of induction circuits disposed on the second side induce the magnetic field component and one or more of the plurality of sensors disposed on the first side sense the strength and the phase of the magnetic field.

16. The magnetic response distribution visualization device according to claim 15, wherein
the information processing circuit selects, as the magnetic response distribution image, either a first magnetic response distribution image generated based on the first operation or a second magnetic response distribution image generated based on the second operation.

17. A security inspection system comprising:
the magnetic response distribution visualization device according to claim 1; and
a thermographic device for performing diagnostic imaging on a person corresponding to the moving object.

18. A magnetic response distribution visualization method comprising:
inducing, from outside a moving object, a magnetic field component that is a component of a magnetic field that satisfies a fundamental equation for magnetic fields, using an induction circuit;
sensing, using a sensor, a strength and a phase of the magnetic field including the magnetic field component altered by the moving object, at a plurality of points in time outside the moving object; and
based on a sensing result of the strength and the phase of the magnetic field, a moving speed of the moving object, and the fundamental equation for magnetic fields, calculating a strength and a phase of the magnetic field at a vicinal position closer to the moving object than the sensor, and generating, based on a calculation result of the strength and the phase of the magnetic field, a magnetic response distribution image that shows a distribution of a response of the moving object to the magnetic field component induced by the induction circuit and is used for security inspection.

* * * * *